(12) United States Patent
Roh et al.

(10) Patent No.: US 9,834,537 B2
(45) Date of Patent: Dec. 5, 2017

(54) COMPOUNDS AS CHLORIDE CHANNEL BLOCKING AGENT

(71) Applicant: Korea Institute of Science and Technology, Seoul (KR)

(72) Inventors: Eun Joo Roh, Seoul (KR); Changjoon Justin Lee, Seoul (KR); Soo Jin Oh, Seoul (KR); Seok Jin Hwang, Gunwi-gun (KR); Jong Hoon Jung, Incheon (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 14/092,151

(22) Filed: Nov. 27, 2013

(65) Prior Publication Data

US 2015/0148550 A1    May 28, 2015

(51) Int. Cl.
| | | |
|---|---|---|
| *C07C 229/56* | (2006.01) | |
| *C07D 333/10* | (2006.01) | |
| *C07D 333/40* | (2006.01) | |
| *C07C 229/58* | (2006.01) | |

(52) U.S. Cl.
CPC .......... *C07D 333/40* (2013.01); *C07C 229/56* (2013.01); *C07C 229/58* (2013.01)

(58) Field of Classification Search
CPC ... A61K 31/381; C07D 333/10; C07C 229/56
USPC .............................. 549/29, 68; 514/438, 447
See application file for complete search history.

(56) References Cited

U.S. PATENT DOCUMENTS

| | | | | |
|---|---|---|---|---|
| 3,856,690 A | * | 12/1974 | Braid ....................... C10M 1/08 | 252/403 |
| 3,856,909 A | * | 12/1974 | Allais et al. .................. | 514/313 |
| 3,963,750 A | | 6/1976 | Goudie | |
| 3,989,746 A | * | 11/1976 | Nohara ................. C07C 17/093 | 514/870 |
| 4,003,747 A | * | 1/1977 | Tsunoda ................. G03C 1/695 | 430/167 |
| 4,021,470 A | * | 5/1977 | Braid ....................... C10M 1/08 | 558/416 |
| 4,307,113 A | | 12/1981 | Anderson | |

FOREIGN PATENT DOCUMENTS

| | | |
|---|---|---|
| KR | 10-0799892 B1 | 1/2008 |
| KR | 10-0892591 | 4/2009 |
| KR | 10-2010-0119757 A | 11/2010 |
| WO | 2004/111017 | 12/2004 |

OTHER PUBLICATIONS

Wangemann et al (1987): STN International HCAPLUS database, Columbus (OH), Accession No. 1987: 489293.*
Wangemann et al (1987): STN International HCAPLUS database, (Columbus, Ohio), Accession No. 1987:489293.*
Oh et al (2013): STN International HCAPLUS database, (Columbus, Ohio), Accession No. 2013:1660683.*
Braid et al (1977): STN International HCAPLUS database, (Columbus, Ohio), Accession No. 1977:520393.*
Moore et al (1961): STN International HCAPLUS database, (Columbus, Ohio), Accession No. 1961:137615.*
Rewcastle et al (1987): STN International HCAPLUS database, Columbus (OH), Accession No. 1987: 176337.*
Tsunoda et al (1977): STN International HCAPLUS database, Columbus (OH), Accession No. 1977: 98985.*
Soo-Jin Oh, et al., "MONNA, a Potent and Selective Blocker for Transmembrane Protein with Unknown Function 16/Anoctamin-1," http:/dx.doi.org/10.1124/mol.113.087502, Nov. 2013, pp. 726-735.
Zeng, Liang, et al. "Efficient Copper-Catalyzed Synthesis of N-Alkylanthranilic Acids via an ortho-Substituent Effect of the Carboxyl Group of 2-Halobenzoic Acids at Room Temperature." Advanced Synthesis & Catalysis 351.10 (2009): 1671-1676. (6 pages in English).

* cited by examiner

*Primary Examiner* — Golam M M Shameem
(74) *Attorney, Agent, or Firm* — NSIP Law

(57) ABSTRACT

Disclosed is a novel compound to function as a calcium-dependent chloride channel blocking agent.

7 Claims, No Drawings

COMPOUNDS AS CHLORIDE CHANNEL BLOCKING AGENT

BACKGROUND (a) Technical Field

The present disclosure relates to a novel compound that functions as a calcium-dependent chloride channel blocking agent.

(b) Background Art

The above information disclosed in this Background section is only for enhancement of understanding of the background of the invention and therefore it may contain information that does not form the prior art that is already known in this country to a person of ordinary skill in the art.

A chloride channel derived from different kinds of cells has a characteristic of being activated by a calcium ion concentration ranging from 0.2 to 5 mM in cytoplasm. The existence of the chloride channel was firstly found in a frog egg cell in the 1980s. It was found in the frog egg cell that, when a calcium-sensitive chloride channel is open due to an increase in calcium ion concentration during fertilization, depolarization of a membrane occurs, which in turn, prevents sperm cells from flowing into the membrane. Thereafter, the existence of a calcium-dependent chloride channel in a variety of neural cells and other cells has been demonstrated.

A chloride channel has different functions depending upon cells from which the chloride channel is derived. Major functions of the chloride channel known in the related art may include epithelial secretion, membrane excitability of cardiac muscle and neuronal cells, conduction of olfactory impulses, pulse control, control of a photoreceptor reaction, or the like. Accordingly, a compound having chloride channel blocking activity may be used as an effective drug for treating, preventing and/or alleviating diseases including: (i) bone diseases related to osteoclasts such as osteoporosis, postmenopausal osteoporosis, Type III osteoporosis, osteolytic bone metastasis associated breast cancer, invasion of osteolytic cancer, Paget's disease of bone, or the like; (ii) tumor cell proliferative diseases such as cancer, prostate cancer, lung cancer, breast cancer, bladder cancer, kidney cancer, colon cancer, stomach cancer, pancreas cancer, ovarian cancer, melanoma, liver cancer, sarcoma, lymphoma, or the like; (iii) diseases related to ocular vascular formation such as wet macular degeneration, age-related macular degeneration (AMD), retinopathy, diabetic retinopathy, proliferative diabetic retinopathy, diabetic macular edema (DME), ischemic retinopathy (i.e., retinal vein occlusion or retinal artery occlusion), retinopathy of prematurity, neovascular glaucoma, corneal neovascularization, or the like; (iv) diseases caused by reduction of intraocular pressure such as ocular hypertension, open angle glaucoma, chronic open angle glaucoma, closed angle glaucoma, ciliary hyperemia caused by closed angle glaucoma, or the like; (v) rheumatoid arthritis; (vi) psoriasis; (vii) sickle-cell anemia, and the like (see International Patent Laid-Open Publication No. 2004/111017).

As such, studies into the various and important functions of the calcium-dependent chloride channel have continued about 20 years since 1980s. However, research into mechanisms relating to physiological functions and control thereof has still been insufficient. Such related conditions continue as an appropriate chloride channel blocking agent has not yet been developed, therefore, the development of a chloride channel blocking agent which exhibits adequate reliability and selectivity is urgently needed.

Under the foregoing circumstances, the present inventors have developed an anthranilic acid compound represented by formula A below, as a calcium-dependent chloride channel blocking agent, which was granted as a patent in Korea with Korean Patent No. 892,591:

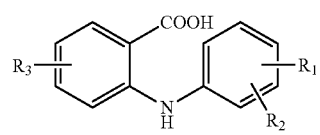

[Formula A]

wherein, $R_1$ and $R_2$ are independently each selected from a group consisting of a hydrogen atom; halogen atom; linear, branched or cyclic alkyl having 5 to 16 carbon atoms; linear or branched substituted alkyl having 1 to 16 carbon atoms; substituted or non-substituted aryl having 6 to 12 carbon atoms; alkoxy having 1 to 8 carbon atoms; substituted alkoxy having 1 to 8 carbon atoms; and a nitro group, provided that $R_1$ and $R_2$ cannot be simultaneously hydrogen atoms; and; $R_3$ is a hydrogen atom or nitro group.

The anthranilic acid compound described in the present invention is a novel compound not disclosed in the foregoing registered patent and has a characteristic in a chemical structure thereof wherein a naphthylamino group having various substituents is substituted at a C2 position of a mother nucleus of anthranilic acid. Alternatively, as compared to the anthranilic acid compound represented by Formula A which is substituted by a phenyl group at a C2 position, the anthranilic acid compound of the present invention having a naphthylamino group substituted at a C2 position has more superior efficacy as a calcium-dependent chloride channel blocking agent.

SUMMARY OF THE DISCLOSURE

The present invention provides a 3-(arylamino)thiophene-2-carboxylic acid compound or 2-(arylamino)anthranilic acid compound.

The present invention also provides a pharmaceutical composition used as a calcium-dependent chloride channel blocking agent that contains the foregoing novel compound as an effective ingredient.

In order to accomplish the above objects, in one aspect, the present invention provides a compound represented by formula 1 below or pharmaceutically acceptable salt compounds thereof:

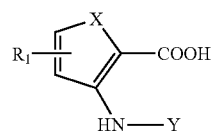

[Formula 1]

wherein X is —S— or —C=C—; Y is —$R_2$ or —$(CH_2)_nR_2$ (wherein n is an integer from 0 to 6); $R_1$ is a hydrogen atom, halogen atom, nitro, $C_1$-$C_6$ alkyl or $C_1$-$C_6$ haloalkyl group; and $R_2$ is a phenyl or naphthyl group substituted or non-substituted by 1 to 3 substituents selected from a group consisting of halo, nitro, $C_1$-$C_6$ alkyl, $C_1$-$C_6$ alkoxy and $C_1$-$C_6$ haloalkyl group, provided that a compound having a substituted or non-substituted phenyl group as $R_2$ when X is —C=C—, is excluded.

In a preferred embodiment, the present invention provides a pharmaceutical composition useful as a calcium-dependent chloride channel blocking agent that contains the compound represented by formula 1 or pharmaceutically acceptable salt compounds thereof as an active ingredient.

Since the inventive compound has activity as a calcium-dependent channel blocking agent, it may be effective in the treatment, prevention or alleviation of diseases related to chloride channel function.

Such diseases possibly treated, prevented or alleviated using the chloride channel blocking agent may include, for example: bone diseases related to osteoclasts such as osteoporosis, postmenopausal osteoporosis, Type III osteoporosis, osteolytic bone metastasis associated breast cancer, invasion of osteolytic cancer, Paget's disease of bone, or the like; tumor cell proliferative diseases such as cancer, prostate cancer, lung cancer, breast cancer, bladder cancer, kidney cancer, colon cancer, stomach cancer, pancreas cancer, ovarian cancer, melanoma, liver cancer, sarcoma, lymphoma, or the like; diseases related to ocular vascular formation such as wet macular degeneration, age-related macular degeneration (AMD), retinopathy, diabetic retinopathy, proliferative diabetic retinopathy, diabetic macular edema (DME), ischemic retinopathy (i.e., retinal vein occlusion or retinal artery occlusion), retinopathy of prematurity, neovascular glaucoma, corneal neovascularization, or the like; diseases caused by reduction of intraocular pressure such as ocular hypertension, open angle glaucoma, chronic open angle glaucoma, closed angle glaucoma, ciliary hyperemia caused by closed angle glaucoma, or the like; rheumatoid arthritis; psoriasis; sickle-cell anemia, and the like.

DETAILED DESCRIPTION

Hereinafter reference will now be made in detail to various embodiments of the present invention, examples of which are described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The present invention provides a compound represented by the following formula 1 or pharmaceutically acceptable salt compounds thereof, or a pharmaceutical composition that contains the foregoing compound as an active ingredient:

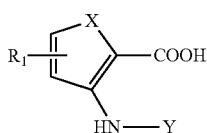

[Formula 1]

wherein X is —S— or —C=C—; Y is —$R_2$ or —$(CH_2)_nR_2$ (wherein n is an integer from 0 to 6); $R_1$ denotes a hydrogen atom, halogen atom, nitro, $C_1$-$C_6$ alkyl or $C_1$-$C_6$ haloalkyl group; and $R_2$ denotes a phenyl or naphthyl group substituted or non-substituted by 1 to 3 substituents selected from a group consisting of halo, nitro, $C_1$-$C_6$ alkyl, $C_1$-$C_6$ alkoxy and $C_1$-$C_6$ haloalkyl group, provided that a compound having a substituted or non-substituted phenyl group as $R_2$ when X is —C=C—, is excluded.

The compound represented by formula 1 according to the present invention may form a pharmaceutically acceptable salt by any conventional method known in the related art. For instance, pharmaceutically acceptable acidic salts of the compound represented by formula 1 using a non-toxic inorganic acid such as hydrochloric acid, bromic acid, sulfonic acid amidosulfuric acid, phosphoric acid, nitric acid, etc., or a non-toxic organic acid such as propionic acid, succinic acid, glycolic acid, stearic acid, lactic acid, tartaric acid, citric acid, para-toluene sulfonic acid, methane sulfonic acid, etc., may be formed.

Hereinafter, substituents used for defining the compound represented by formula 1 according to the present invention will be described in more detail.

An 'alkyl' group includes all of linear or branched carbon chains having 1 to 6 carbon atoms, and preferably, methyl, ethyl, propyl, isopropyl, butyl, isobutyl, tert-butyl, or the like. An 'alkoxy' group means an alkyl group having carbon bonded oxygen wherein the alkyl group has the same definition as described above. A 'haloalky' group includes all of linear or branched carbon chains having 1 to 13 halogen atoms such as fluoro, chloro, bromo, iodo, etc. and 1 to 6 carbon atoms, and preferably, fluoromethyl, trifluoromethyl, 1,2-dichloroethyl, 1,1-dichloroethyl, pentafluoroethyl, or the like.

With regard to the compound represented by formula 1 according to the present invention, $R_1$ denotes preferably a hydrogen atom, fluorine atom, chlorine atom, nitro, methyl, ethyl, propyl, fluoromethyl, trifluoromethyl, dichloroethyl or hexafluoroethyl group; and $R_2$ denotes preferably a phenyl, 4-halophenyl, 2-trifluoromethylphenyl, 4-trifluoromethylphenyl, 2,4-di(trifluoromethyl)phenyl, 2,4-difluorophenyl, 2,6-difluorophenyl, 3,4-dichlorophenyl, 4-nitrophenyl, 4-methylphenyl, 4-methoxyphenyl, 1-naphthyl, 2-naphthyl, 4-halo-1-naphthyl, 2-trifluoromethylnaphthyl, 4-trifluoromethylnaphthyl, 2,4-di(trifluoromethyl)naphthyl, 2,4-difluoronaphthyl, 2,6-difluoronaphthyl, 3,4-dichloronaphthyl, 4-nitronaphthyl, 4-methyl naphthyl, 4-methoxynaphthyl, 5-methoxynaphthyl, 4-nitro-2-naphthyl, 4-methyl-2-naphthyl, 1-methoxy-2-naphthyl, 4-methoxy-2-naphthyl, or 5-methoxy-2-naphthyl group.

Further, the compound represented by formula 1 according to the present invention may be classified into 3-(arylamino)thiophene-2-carboxylic acid compounds represented by formula 1a and 2-(arylamino)anthranilic acid compounds represented by formula 1b.

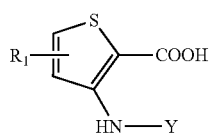

[Formula 1a]

wherein Y is —$R_2$ or —$(CH_2)_nR_2$ (wherein n is an integer from 0 to 6); and $R_1$ and $R_2$ have the same meanings as defined in formula 1, respectively.

Further, in the compound represented by formula 1 a: preferably,

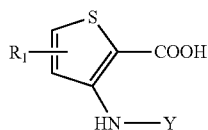
[Formula 1a]

Y is —$R_2$ or —$(CH_2)_nR_2$ (wherein n is an integer from 0 to 6); $R_1$ denotes a hydrogen atom, fluorine atom, chlorine atom, nitro, methyl, ethyl, propyl, fluoromethyl, trifluoromethyl, dichloroethyl or hexafluoroethyl group; and $R_2$ denotes a phenyl, 4-halophenyl, 2-trifluoromethylphenyl, 4-trifluoromethylphenyl, 2,4-di(trifluoromethyl)phenyl, 2,4-difluorophenyl, 2,6-difluorophenyl, 3,4-dichlorophenyl, 4-nitrophenyl, 4-methylphenyl, 4-methoxyphenyl, 1-naphthyl, 2-naphthyl, 4-halo-1-naphthyl, 2-trifluoromethylnaphthyl, 4-trifluoromethylnaphthyl, 2,4-di(trifluoromethyl)naphthyl, 2,4-difluoronaphthyl, 2,6-difluoronaphthyl, 3,4-dichloronaphthyl, 4-nitronaphthyl, 4-methylnaphthyl, 4-methoxynaphthyl, 5-methoxynaphthyl, 4-nitro-2-naphthyl, 4-methyl-2-naphthyl, 1-methoxy-2-naphthyl, 4-methoxy-2-naphthyl or 5-methoxy-2-naphthyl group.

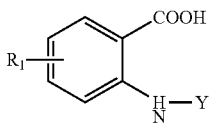
[Formula 1b]

wherein Y is —$R_2$ or —$(CH_2)_nR_2$ (wherein n is an integer from 0 to 6); and $R_1$ has the same meanings as defined in formula 1 while $R_2$ is a substituted or non-substituted naphthyl group.

Further, in the compound represented by formula 1b: preferably,

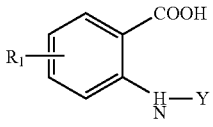
[Formula 1b]

wherein Y is —$R_2$ or —$(CH_2)_nR_2$ (wherein n is an integer from 0 to 6);

$R_1$ denotes a hydrogen atom, fluorine atom, chlorine atom, nitro, methyl, ethyl, propyl, fluoromethyl, trifluoromethyl, dichloroethyl or hexafluoroethyl group; and $R_2$ denotes 1-naphthyl, 2-naphthyl, 4-halo-1-naphthyl, 2-trifluoromethylnaphthyl, 4-trifluoromethylnaphthyl, 2,4-di(trifluoromethyl)naphthyl, 2,4-difluoronaphthyl, 2,6-difluoronaphthyl, 3,4-dichloronaphthyl, 4-nitronaphthyl, 4-methylnaphthyl, 4-methoxynaphthyl, 5-methoxynaphthyl, 4-nitro-2-naphthyl, 4-methyl-2-naphthyl, 1-methoxy-2-naphthyl, 4-methoxy-2-naphthyl or 5-methoxy-2-naphthyl group.

Particular examples of the compound represented by formula 1 according to the present invention may include: compound No. 1: 3-(4-fluorophenylamino)thiophene-2-carboxylic acid, compound No. 2: 3-(4-chlorophenylamino)thiophene-2-carboxylic acid, compound No. 3: 3-(4-boromophenylamino)thiophene-2-carboxylic acid, compound No. 4: 3-(4-(trifluoromethyl)phenylamino)thiophene-2-carboxylic acid, compound No. 5: 3-(4-methylphenylamino)thiophene-2-carboxylic acid, compound No. 6: 3-(4-methoxyphenylamino)thiophene-2-carboxylic acid, compound No. 7: 3-(2-(trifluoromethyl)phenylamino)thiophene-2-carboxylic acid, compound No. 8: 3-(2,4-bis(trifluoromethyl)phenylamino)thiophene-2-carboxylic acid, compound No. 9: 3-(2,4-difluorophenylamino)thiophene-2-carboxylic acid, compound No. 10: 3-(2,6-difluorophenylamino)thiophene-2-carboxylic acid, compound No. 11: 3-(3,5-dichlorophenylamino)thiophene-2-carboxylic acid, compound No. 12: 3-(3-fluoro-4-methoxyphenylamino)thiophene-2-carboxylic acid, compound No. 13: 3-(1-naphthylamino)thiophene-2-carboxylic acid, compound No. 14: 3-((4-methoxy)-1-naphthylamino)thiophene-2-carboxylic acid, compound No. 15: 3-((5-methoxy)-1-naphthylamino)thiophene-2-carboxylic acid, compound No. 16: 3-((4-nitro)-1-naphthylamino)thiophene-2-carboxylic acid, compound No. 17: 3-((4-chloro)-1-naphthylamino)thiophene-2-carboxylic acid, compound No. 18: 3-(2-naphthylamino)thiophene-2-carboxylic acid, compound No. 19. 3-((4-methoxy)-2-naphthylamino)thiophene-2-carboxylic acid, compound No. 20: 5-nitro-3-(4-chlorophenylamino)thiophene-2-carboxylic acid, compound No. 21: 5-nitro-3-(4-bromophenylamino)thiophene-2-carboxylic acid, compound No. 22: 5-nitro-3-(4-iodophenylamino)thiophene-2-carboxylic acid, compound No. 23: 5-nitro-3-((4-methoxy)-2-naphthylamino)thiophene-2-carboxylic acid, compound No. 24: 4-nitro-3-(4-chlorophenylamino)thiophene-2-carboxylic acid, compound No. 25: 4-nitro-3-(4-bromophenylamino)thiophene-2-carboxylic acid, compound No. 26: N-(4-fluorophenyl)-3-nitroanthranilic acid, compound No. 27: N-(4-chlorophenyl)-3-nitroanthranilic acid, compound No. 28: N-naphthyl-3-nitroanthranilic acid, compound No. 29: N-((4-chloro)naphthyl)-3-nitroanthranilic acid, compound No. 30: N-(2-naphthyl)-3-nitroanthranilic acid, compound No. 31: N-naphthyl-4-nitroanthranilic acid, compound No. 32: N-((4-fluoro)naphthyl)-4-nitroanthranilic acid, compound No. 33: N-((4-chloro)naphthyl)-4-nitroanthranilic acid, compound No. 34: N-((4-bromo)naphthyl)-4-nitroanthranilic acid, compound No. 35: N-((4-nitro)naphthyl)-4-nitroanthranilic acid, compound No. 36: N-((4-methoxy)naphthyl)-4-nitroanthranilic acid, compound No. 37: N-(2-naphthyl)-4-nitroanthranilic acid, compound No. 38: N-((1-methoxy)-2-naphthyl)-4-nitroanthranilic acid, compound No. 39: N-((4-methoxy)-2-naphthyl)-4-nitroanthranilic acid, compound No. 40: N-naphthyl-5-nitroanthranilic acid, compound No. 41: N-((4-fluoro)naphthyl)-5-nitroanthranilic acid, compound No. 42: N-((4-chloro)naphthyl)-5-nitroanthranilic acid, compound No. 43: N-((4-bromo)naphthyl)-5-nitroanthranilic acid, compound No. 44: N-((4-iodo)naphthyl)-5-nitroanthranilic acid, compound No. 45: N-((2-methoxy)naphthyl)-5-nitroanthraniic acid, compound No. 46: N-((3-methoxy)naphthyl)-5-nitroanthranilic acid, compound No. 47: N-((4-methoxy)naphthyl)-5-nitroanthranilic acid, compound No. 48: N-((5-methoxy)naphthyl)-5-nitroanthranilic acid, compound No. 49: N-((6-methoxy)naphthyl)-5-nitroanthranilic acid, compound No. 50: N-((7-methoxy)naphthyl)-5-nitroanthranilic acid, compound No. 51: N-((8-methoxy)naphthyl)-5-nitroanthranilic acid, compound No. 52: N-(2-naphthyl)-5-nitroanthranilic acid, compound No. 53: N-((1-methoxy)-2-naphthyl)-5-nitroanthranilic acid, compound No. 54: N-((3-methoxy)-2-naphthyl)-5-nitroanthranilic acid, compound No. 55: N-((4-methoxy)-2-naphthyl)-5-nitroanthranilic acid, compound No. 56: N-((5-methoxy)-2-naphthyl)-5-nitroanthranilic acid, compound No. 57: N-((6-methoxy)-2-naphthyl)-5-nitroanthranilic acid, compound No. 58: N-((7-methoxy)-2-naphthyl)-5-nitroanthranilic acid, compound No. 59: N-((8-methoxy)-2-naphthyl)-5-nitroanthranilic acid, compound No. 60: N-naphthyl-4-trifluoromethyl anthranilic acid, compound No. 61: N-((4-chloro)naphthyl)-4-trifluoromethyl anthranilic acid, compound No. 62: N-((4-nitro)naphthyl)-4-trifluoromethyl anthranilic acid, compound No. 63: N-(2-naphthyl)-4-trifluoromethyl anthranilic acid.

Meanwhile, since the compound represented by formula 1 or pharmaceutically acceptable salts thereof according to the present invention are very effective as a calcium-dependent chloride channel blocking agent, the present invention also claims a pharmaceutical composition that contains the novel compound represented by formula 1 as an effective ingredient. The pharmaceutical composition according to the present invention, which contains the compound represented by formula 1 or pharmaceutically acceptable salts thereof as an effective ingredient, may be useful for treating, preventing or alleviating diseases or disorders caused by a calcium-dependent chloride channel.

More particularly, the diseases possibly treated, prevented or alleviated through blocking the chloride channel may include: bone diseases related to osteoclasts such as osteoporosis, postmenopausal osteoporosis, Type III osteoporosis, osteolytic bone metastasis associated breast cancer, invasion of osteolytic cancer, Paget's disease of bone, or the like; tumor cell proliferative diseases such as cancer, prostate cancer, lung cancer, breast cancer, bladder cancer, kidney cancer, colon cancer, stomach cancer, pancreas cancer, ovarian cancer, melanoma, liver cancer, sarcoma, lymphoma, or the like; diseases related to ocular vascular formation such as wet macular degeneration, age-related macular degeneration (AMD), retinopathy, diabetic retinopathy, proliferative diabetic retinopathy, diabetic macular edema (DME), ischemic retinopathy (i.e., retinal vein occlusion or retinal artery occlusion), retinopathy of prematurity, neovascular glaucoma, corneal neovascularization, or the like; diseases caused by reduction of intraocular pressure such as ocular hypertension, open angle glaucoma, chronic open angle glaucoma, closed angle glaucoma, ciliary hyperemia caused by closed angle glaucoma, or the like; rheumatoid arthritis; psoriasis; sickle-cell anemia, and the like.

The pharmaceutical composition of the present invention may further include, in addition to the compound represented by formula 1 or pharmaceutically acceptable salts thereof, a conventional non-toxic and pharmaceutically acceptable carrier, reinforcing agent and/or excipient, or the like added thereto, so as to prepare a typical formulation for oral or parenteral administration such as tablets, capsules, troches, liquids, suspensions, or the like. Further, an administration amount ('dose') of the compound represented by formula 1 to a human being may defer to age, body weight, gender, administration type, physical conditions and/or severity of disease of a patient. In a case of an adult patient having a body weight of 70 kg, a dose of the foregoing compound ranges, in general, from 0.01 to 400 mg/day and, according to the judgment of a physician or pharmacist, the compound may be administered once or partly at a constant interval in several times everyday.

The compound represented by formula 1 according to the present invention may be formed by any one of preparation methods illustrated in the following schemes 1, 2 and 3.

A first preparation method of the present invention is shown in reaction scheme 1 below:

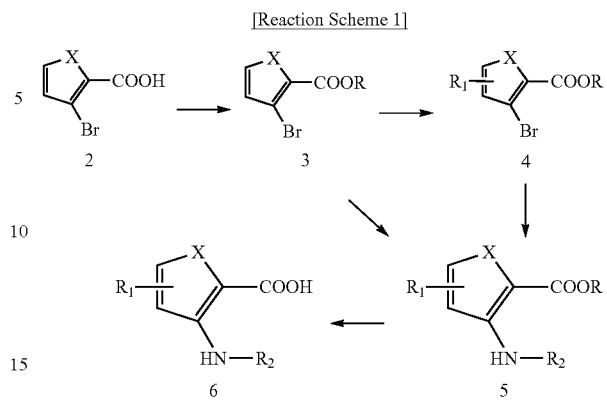

[Reaction Scheme 1]

wherein X, $R_1$, and $R_2$ are respectively the same as defined in formula 1, and R denotes a $C_1$-$C_6$ alkyl group.

The preparation method according to the reaction scheme 1 may include: (i) esterifying a carboxylic acid compound represented by formula 2 to prepare an ester compound represented by formula 3; (ii) introducing a variety of $R_1$ substituents as well as an amine group (—$NHR_2$) into an aromatic ring of the ester compound represented by formula 3 to prepare an aminoester compound represented by formula 5; and (iii) hydrolyzing the aminoester compound represented by formula 5 to produce an aminocarboxylic acid compound represented by formula 6.

The esterifying process (i) may be executed through an esterification reaction. The esterification reaction is a conventional method used in the art and not particularly limited. As a general method, Fischer esterification using an acid catalyst and alcohol solvent may be mostly employed. In embodiments of the present invention, an esterification method using chlorotrimethylsilane (TMSCI) was adopted in consideration of reactivity and mild reaction conditions.

The introducing process (ii) includes introduction of an $R_1$ substituent and introduction of an amine group (—$NHR_2$), and both of these introductions may be executed simultaneously in a single container or, otherwise, conducted in sequential order. According to the present invention, the order of introducing $R_1$ substituent and amine group (—$NHR_2$) is not particularly limited.

A representative $R_1$ substituent is a nitro group ($NO_2$) and an introduction method thereof is as follows: using sulfuric acid ($H_2SO_4$) as a solvent and reagent and sodium nitrate ($NaNO_3$) as a nitration agent, nitration may be executed while maintaining a temperature of −20° C. to 10° C. to reduce a side reaction (Nitration), so as to introduce the nitro group into an aromatic ring.

Introduction of an amine group (-$NHR_2$) may be executed through formation of a complex with a proper ligand under a catalyst. In this case, it is important to firstly react the ligand with a metal catalyst to form a complex and, preferably, refluxing is conducted under a proper organic solvent. The catalyst useable herein is a catalytic material to accelerate the binding of a halogen (Br) atom to an amino group and a representative example of the catalyst may be a palladium catalyst such as palladium acetate (Pd(OAc)$_2$), tris(dibenzylidinacetone)dipalladium (Pd$_2$(dba)$_3$), tris(dibenzylidinacetone)dipalladium chloroform complex (Pd$_2$(dba)$_3$.CHCl$_3$), or the like. Further, the ligand used herein may include a bis-phosphine compound, for example, 1,1'-diphenylphosphinoferrocene (dppf) or 2,2'-bis(diphenylphosphino)-1,1'-binaphthalene (BINAP), or the like. Further, a base such as alkali-earth metal salts, representatively, cesium carbonate ($Cs_2CO_3$) may be used. Further, the reaction solvent may include any organic solvent if it can dissolve a reactant material, and most preferably, toluene is used.

The hydrolyzing process (iii) may be executed through hydrolysis. For hydrolysis, any metal compound capable of reacting with an alkyl ester group to generate a carboxyl group may be used and preferably include, at least one selected from a group consisting of alkaline metal hydroxides and alkali-earth metal hydroxides. More particularly, lithium hydroxide (LiOH), potassium hydroxide (KOH), sodium hydroxide (NaOH), etc., may be used. Further, the reaction solvent may be desirably selected and used, in particular, may include at least one selected from a group consisting of water, tetrahydrofuran and methanol. In embodiments of the present invention, a mixed solvent including $THF/MeOH/H_2O$ in a ratio by volume of 5:3:2 was used. Further, the hydrolyzing process was sufficiently performed at room temperature or reflux temperature for 1-24 hours.

A second preparation method according to the present invention is shown in reaction scheme 2 below:

[Reaction Scheme 2]

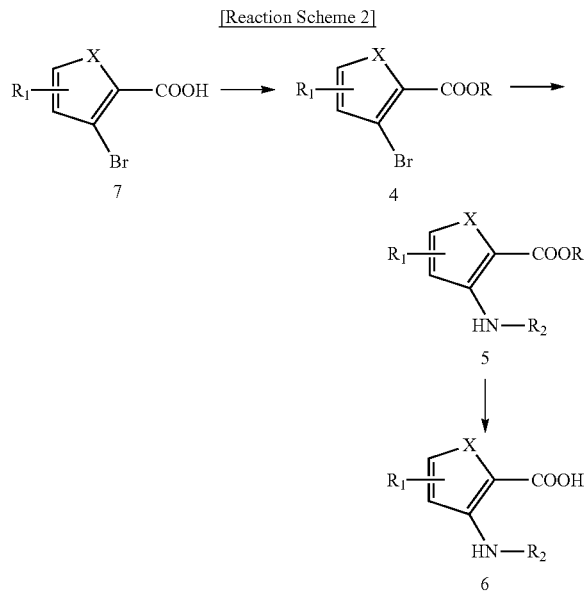

wherein X, $R_1$, and $R_2$ are respectively the same as defined in formula 1, and R denotes a $C_1$-$C_6$ alkyl group.

The preparation method according to the reaction scheme 2 may include: (i) esterifying a carboxylic acid compound represented by formula 7 to prepare an ester compound represented by formula 4; (ii) introducing an amine group (—$NHR_2$) into an aromatic ring of the ester compound represented by formula 4 to prepare an aminoester compound represented by formula 5; and (iii) hydrolyzing the aminoester compound represented by formula 5 to produce an aminocarboxylic acid compound represented by formula 6.

The esterifying, amine group (—$NHR_2$) introducing and hydrolyzing processes in the preparation method shown in scheme 2 may be executed by appropriately applying the preparation method shown in scheme 1, which is obviously understood by those skilled in the art.

A third preparation method according to the present invention is shown in reaction scheme 3 below:

[Reaction Scheme 3]

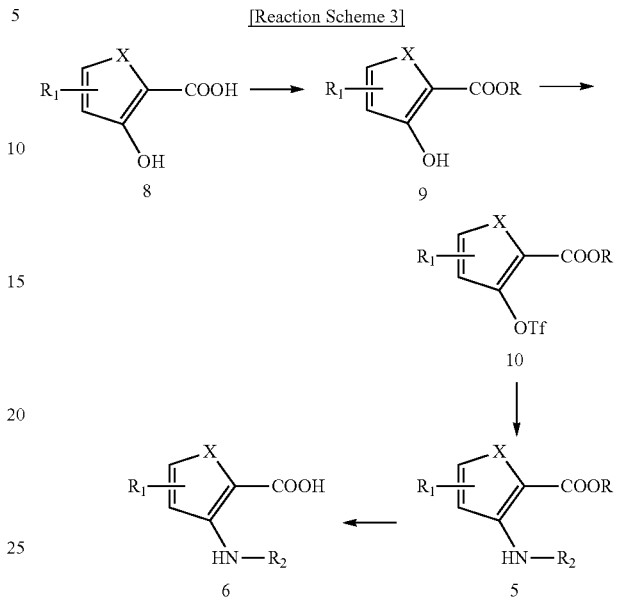

wherein X, $R_1$, and $R_2$ are respectively the same as defined in formula 1, and, R denotes a $C_1$-$C_6$ alkyl group.

The preparation method according to the reaction scheme 3 may include: (i) esterifying a carboxylic acid compound represented by formula 8 to prepare an ester compound represented by formula 9; (ii) substituting triflate for a hydroxyl group in the ester compound represented by formula 9 to prepare a trifloxyester compound represented by formula 10; (iii) introducing an amine group (—$NHR_2$) into an aromatic ring of the trifloxyester compound represented by formula 10 to prepare an aminoester compound represented by formula 5; and (iv) hydrolyzing the aminoester compound represented by formula 5 to produce an aminocarboxylic acid compound represented by formula 6.

The esterifying, amine group (—$NHR_2$) introducing and hydrolyzing processes in the preparation method shown in scheme 3 may be executed by appropriately applying the preparation method shown in scheme 1, which is obviously understood by those skilled in the art. The triflate substitution is conducted using a pyridine base and trifluoromethane sulfonic acid anhydride. As a reaction solvent, any conventional organic solvent may be used and, in an embodiment of the present invention, dichloromethane was adopted.

A fourth preparation method according to the present invention is shown in reaction scheme 4 below:

[Reaction Scheme 4]

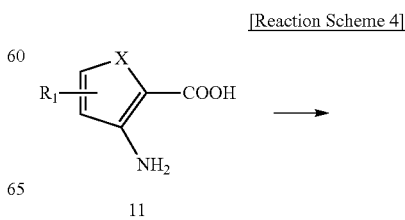

-continued

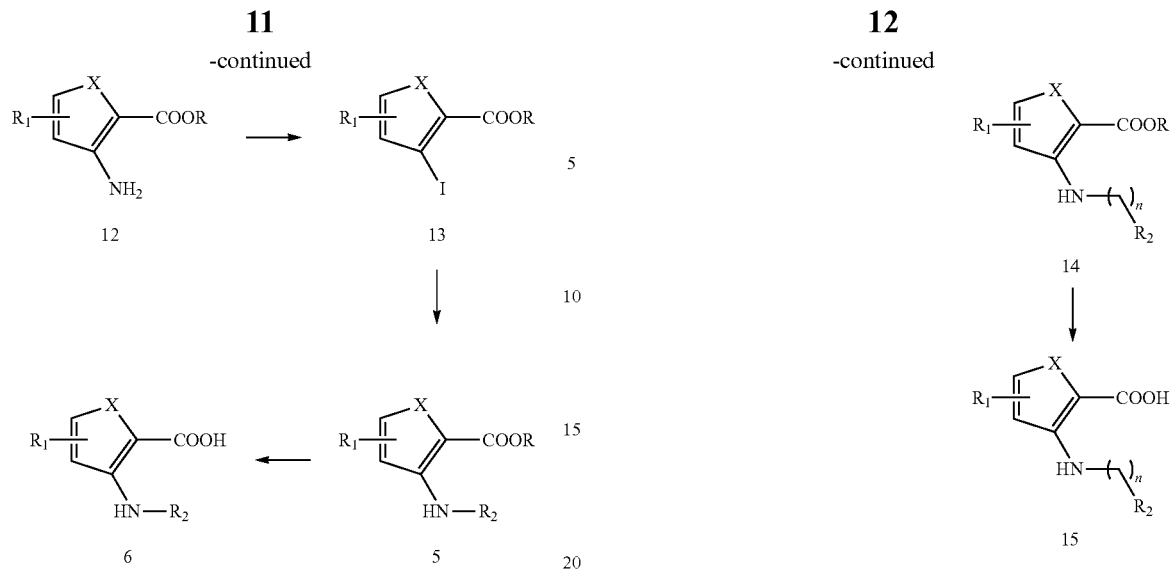

wherein X, $R_1$, and $R_2$ are respectively the same as defined in formula 1, and R denotes a $C_1$-$C_6$ alkyl group.

The preparation method according to the reaction scheme 4 may include: (i) esterifying a carboxylic acid compound represented by formula 11 to prepare an ester compound represented by formula 12; (ii) introducing an iodine (I) into an aromatic ring of the ester compound represented by formula 12 to prepare a halogen ester compound represented by formula 13; (iii) introducing an amine group (—$NHR_2$) into an aromatic ring of the halogen ester compound represented by formula 13 to prepare an aminoester compound represented by formula 5; and (iv) hydrolyzing the aminoester compound represented by formula 5 to produce an aminocarboxylic acid compound represented by formula 6.

The amine group (—$NHR_2$) introducing and hydrolyzing processes in the preparation method shown in scheme 4 may be executed by appropriately applying the preparation method shown in scheme 1, which is obviously understood by those skilled in the art. The esterifying process is conducted using a triethylamine base and dimethyl sulfate. As a reaction solvent, any conventional organic solvent may be used and, in an embodiment of the present invention, dimethylformamide was adopted. The introduction of iodine (I), called 'Sandmeyer' reaction, is conducted using sodium nitrite and potassium iodide. Further, diluted hydrochloric acid, which is a solvent and reactant material, is used as a reaction solvent.

A fifth preparation method according to the present invention is shown in reaction scheme 5 below:

wherein X, $R_1$, and $R_2$ have the same meanings as defined in formula 1, R denotes a $C_1$-$C_6$ alkyl group, and n is an integer from 0 to 6.

The preparation method according to the reaction scheme 5 may include: (i) esterifying a carboxylic acid compound represented by formula 11 to prepare an ester compound represented by formula 12; (ii) alkylating an amine group of the ester compound represented by formula 12 to prepare an alkylaminoester compound represented by formula 14; and (iii) hydrolyzing the alkylaminoester compound represented by formula 14 to produce an alkylaminocarboxylic acid compound represented by formula 15.

The esterifying and hydrolyzing processes in the preparation method according to the reaction scheme 5 may be executed by appropriately applying the preparation method according to scheme 1, which is obviously understood by those skilled in the art. The alkylation of the amine is conducted using a sodium iodide base and an aromatic alkyl bromide. As a reaction solvent, a conventional organic solvent may be used and, in an embodiment of the present invention, dimethylformamide was adopted.

A sixth preparation method according to the present invention is shown in reaction scheme 6 below:

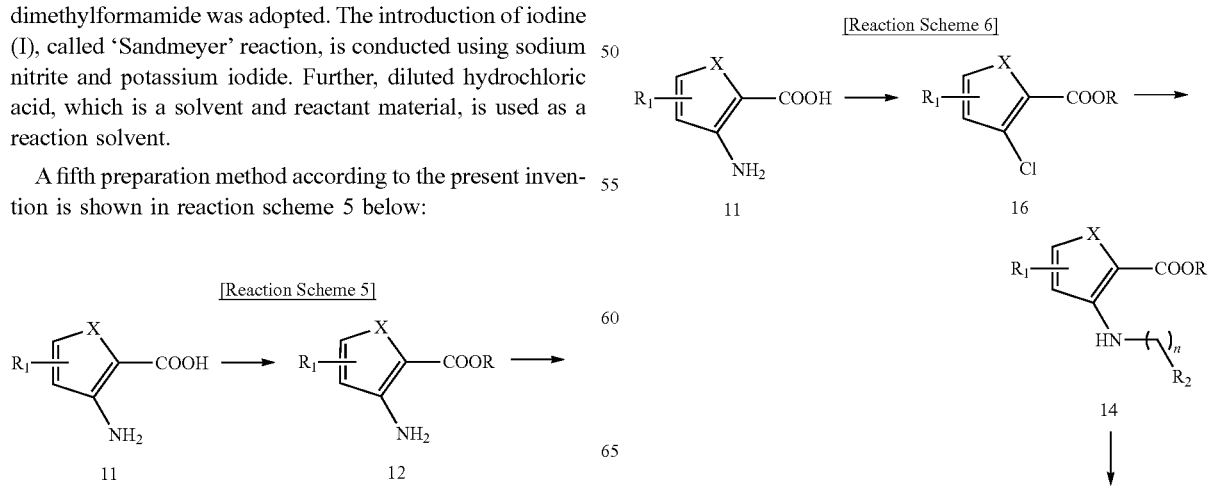

-continued

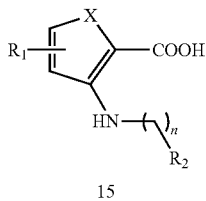

wherein X, $R_1$, and $R_2$ are respectively the same as defined in formula 1, R denotes a $C_1$-$C_6$ alkyl group, and n is an integer from 0 to 6.

The preparation method according to the reaction scheme 6 may include: (i) esterifying and halogenating a carboxylic acid compound represented by formula 11 to prepare a halogen ester compound represented by formula 16; (ii) introducing an alkylamine group (—NH(CH$_2$)$_n$—R$_2$) into an aromatic ring of the ester compound represented by formula 16 to prepare an alkylaminoester compound represented by formula 14; and (iii) hydrolyzing the alkylaminoester compound represented by formula 14 to produce an alkylaminocarboxylic acid compound represented by formula 15.

The esterifying and hydrolyzing processes in the preparation method according to the reaction scheme 6 may be executed by appropriately applying the preparation method according to scheme 1, which is obviously understood by those skilled in the art. The introduction of the alkylamine group is conducted using a potassium carbonate base and an aromatic alkylamine. As a reaction solvent, a conventional organic solvent may be used and, in an embodiment of the present invention, dimethylformamide was adopted.

The present invention as described above will be more concretely explained according to the following examples and experimental examples, however, these examples and experimental examples are not intended to limit the present invention.

EXAMPLES

Example 1

Preparation of 3-(arylamino)thiophene-2-carboxylic acid (1-1) Preparation of 3-bromothiophene-2-carboxylic acid methylester

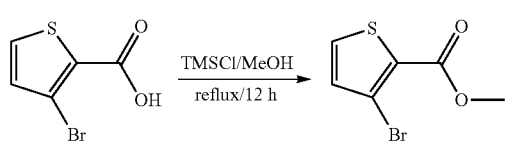

By refluxing 3-bromothiophene-2-carboxylic acid and trimethylsilyl chloride (TMSCl) in a methanol solvent for 12 hours, 3-bromothiophene-2-carboxylic acid methylester was prepared.
Yield: 87%
White solid
$^1$H-NMR (400 MHz, CDCl$_3$) δ 7.46(d, J=5.2 Hz, 1H), 7.10(d, J=5.2 Hz, 1H), 3.90(s, 3H)

(1-2) Preparation of 3-(arylamino)thiophene-2-carboxylic acid methylester

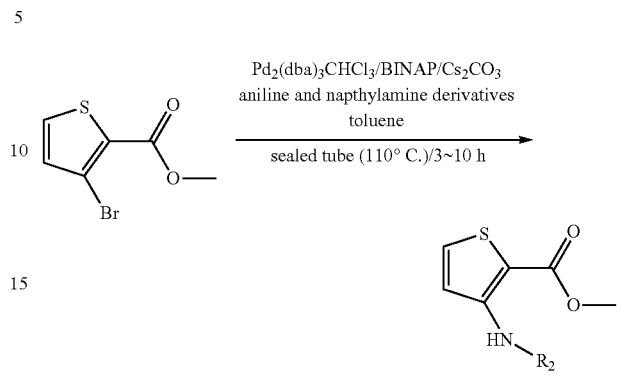

After dissolving 3-bromothiophene-2-carboxylic acid methylester in a toluene solvent within a closed reactor, a tris(dibenzylidineacetone)dipalladium.chloroform complex (Pd$_2$(dba)$_3$.CHCl$_3$) as a palladium catalyst, 2,2'-bis(diphenylphosphino)-1,1'-binaphthalene (BINAP) as a ligand, cesium carbonate (Cs$_2$CO$_3$) as a base, and a variety of amine derivatives represented by R$_2$NH$_2$ were added thereto, followed by heating and reacting the mixture at a temperature of 110° C. to prepare 3-(arylamino)thiophene-2-carboxylic acid methylester.

(1-3) Preparation of 3-(arylamino)thiophene-2-carboxylic acid

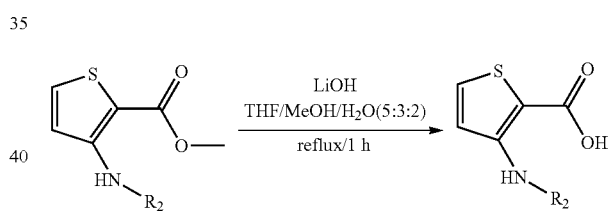

After adding 3-(arylamino)thiophene-2-carboxylic acid methylester and LiOH to a mixed solvent including tetrahydrofuran:methanol:water in a ratio by volume of 5:3:2, the mixture was refluxed to prepare 3-(arylamino)thiophene-2-carboxylic acid.

The compound represented by formula 1 prepared according to a representative synthetic method in Example 1 may include:

Compound No. 1: 3-(4-fluorophenylamino)thiophene-2-carboxylic acid
Yield: 70.5%
Yellow solid
$^1$H-NMR (400 MHz, DMSO-d$_6$) δ 8.79(bs, 1H), 7.72(d, J=5.5 Hz, 1H), 7.26-7.22(m, 2H), 7.18-7.14(m, 2H), 7.06(d, J=5.5 Hz, 1H)

Compound No. 2: 3-(4-chlorophenylamino)thiophene-2-carboxylic acid
Yield: 92.3%
Beige solid
$^1$H-NMR (400 MHz, DMSO-d$_6$) δ 8.89(bs, 1H), 7.76(d, J=5.5 Hz, 1H), 7.35-7.33(m, 2H), 7.24-7.22(m, 2H), 7.16(d, J=5.5 Hz, 1H)

Compound No. 3: 3-(4-bromophenylamino)thiophene-2-carboxylic acid

Yield: 67.3%

Brown solid $^1$H-NMR (400 MHz, DMSO-$d_6$) δ 8.92(bs, 1H), 7.76(d, J=5.5 Hz, 1H), 7.47-7.44(m, 2H), 7.18-7.16(m, 3H)

Compound No. 4: 3-(4-(trifluoromethyl)phenylamino)thiophene-2-carboxylic acid

Yield: 80.7%

Brown solid $^1$H-NMR (400 MHz, DMSO-$d_6$) δ 9.17(bs, 1H), 7.82(d, J=5.5 Hz, 1H), 7.62(d, J=8.7 Hz, 2H), 7.36-7.32(m, 3H)

Compound No. 5: 3-(4-methylphenylamino)thiophene-2-carboxylic acid

Yield: 84.8%

Black solid $^1$H-NMR (400 MHz, DMSO-$d_6$) δ 8.76(bs, 1H), 7.71(d, J=5.4 Hz, 1H), 7.15-7.08(m, 5H), 2.26(s, 3H)

Compound No. 6: 3-(4-methoxyphenylamino)thiophene-2-carboxylic acid

Yield: 47.5%

Ivory solid $^1$H-NMR (400 MHz, DMSO-$d_6$) δ 8.68(bs, 1H), 7.66(d, J=5.5 Hz, 1H), 7.15(m, 2H), 6.94-6.91(m, 3H), 3.74(s, 3H)

Compound No. 7: 3-(2-(trifluoromethyl)phenylamino)thiophene-2-carboxylic acid

Yield: 85.8%,

Ivory solid $^1$H-NMR (400 MHz, CDCl$_3$) δ 9.03(bs, 1H), 7.66(d, J=7.8 Hz, 1H), 7.51-7.50(m, 2H), 7.48(d, J=5.5 Hz, 1H), 7.19-7.15(m, 1H), 7.03(d, J=5.5 Hz, 1H)

Compound No. 8: 3-(2,4-bis(trifluoromethyl)phenylamino)thiophene-2-carboxylic acid Yield: 45.9%, Ivory solid $^1$H-NMR (400 MHz, CDCl$_3$) δ 9.30(bs, 1H), 7.90(s, 1H), 7.74(d, J=8.7 Hz, 1H), 7.61(d, J=8.7 Hz, 1H), 7.58(d, J=5.5 Hz, 1H), 7.17(d, J=5.5 Hz, 1H)

Compound No. 9: 3-(2,4-difluorophenylamino)thiophene-2-carboxylic acid

Yield: 91.0%

Violet solid $^1$H-NMR (400 MHz, CDCl$_3$) δ 8.44(bs, 1H), 7.46(d, J=5.4 Hz, 1H), 7.35-7.29(m, 1H), 6.96-6.85(m, 1H), 6.83(d, J=5.5 Hz, 1H)

Compound No. 10: 3-(2,6-difluorophenylamino)thiophene-2-carboxylic acid

Yield: 75.6%

White solid $^1$H-NMR (400 MHz, DMSO-$d_6$) δ 8.40(bs, 1H), 7.65(d, J=5.5 Hz, 1H), 7.31-7.29(m, 1H), 7.24-7.19(m, 2H), 6.47-6.44(m, 1H)

Compound No. 11. 3-(3,5-dichlorophenylamino)thiophene-2-carboxylic acid

Yield: 39.4%

Yellow solid $^1$H-NMR (400 MHz, DMSO-$d_6$) δ 8.98(bs, 1H), 7.81(d, J=5.4 Hz, 1H), 7.26(d, J=5.4 Hz, 1H), 7.22(bs, 2H), 7.11(bs, 1H)

Compound No. 12: 3-(3-fluoro-4-methoxyphenylamino)thiophene-2-carboxylic acid

Yield: 75.6%

Yellow solid $^1$H-NMR (400 MHz, CDCl$_3$) δ 8.54(bs, 1H), 7.44(d, J=5.5 Hz, 1H), 7.01-6.97(m, 1H), 6.96-6.91(m, 3H), 3.90(s, 3H)

Compound No. 13: 3-(1-naphthylamino)thiophene-2-carboxylic acid

Yield: 78.0%

Dark brown solid $^1$H-NMR (400 MHz, CDCl$_3$) δ 9.04(bs, 1H), 8.12-8.10(m, 1H), 7.90-7.88(m, 1H), 7.70(dd, J=6.6, 2.5 Hz, 1H), 7.58-7.52(m, 2H), 7.49-7.44(m, 2H), 7.42(d, J=5.5 Hz, 1H), 6.86(d, J=5.5 Hz, 1H)

Compound No. 14: 3-((4-methoxy)-1-naphthylamino)thiophene-2-carboxylic acid

Yield: 56.9%

Brown solid $^1$H-NMR (400 MHz, DMSO-$d_6$) δ 8.89(bs, 1H), 8.22(dd, J=8.5, 1.4 Hz, 1H), 7.92(dd, J=8.3, 1.1 Hz, 1H), 7.62(d, J=5.5 Hz, 1H), 7.60-7.55(m, 2H), 7.41(d, J=8.2 Hz, 1H), 6.98(d, J=8.3 Hz, 1H), 6.59(d, J=5.5 Hz, 1H), 3.99(s, 3H)

Compound No. 15: 3-((5-methoxy)-1-naphthylamino)thiophene-2-carboxylic acid

Yield: 91.6%

White solid $^1$H-NMR (400 MHz, DMSO-$d_6$) δ 9.34(bs, 1H), 7.93(dd, J=6.9, 2.3 Hz, 1H), 7.74(d, J=5.5 Hz, 1H), 7.58(d, J=8.5 Hz, 1H), 7.52(d, J=7.7 Hz, 1H), 7.50-7.45(m, 2H), 7.05(d, J=7.6 Hz, 1H), 7.02(d, J=5.5 Hz, 1H), 3.99(s, 3H)

Compound No. 16: 3-((4-nitro)-1-naphthylamino)thiophene-2-carboxylic acid

Yield: 34.0%,

Orange solid $^1$H-NMR (400 MHz, DMSO-$d_6$) δ 10.19(bs, 1H), 8.80(d, J=8.7 Hz, 1H), 8.49(d, J=8.8 Hz, 1H), 8.40(d, J=8.4 Hz, 1H), 8.01(d, J=5.4 Hz, 1H), 7.96-7.92(m, 1H), 7.87-7.83(m, 1H), 7.56(d, J=5.4 Hz, 1H), 7.48(d, J=8.8 Hz, 1H)

Compound No. 17: 3-((4-chloro)-1-naphthylamino)thiophene-2-carboxylic acid

Yield: 46.1%

Yellow solid $^1$H-NMR (400 MHz, DMSO-$d_6$) δ 9.40(bs, 1H), 8.23(d, J=8.0 Hz, 1H), 8.12(d, J=8.2 Hz, 1H), 7.79-7.71(m, 3H), 7.67(d, J=8.1 Hz, 1H), 7.46(d, J=8.1 Hz, 1H), 7.05(d, J=5.5 Hz, 1H)

Compound No. 18: 3-(2-naphthylamino)thiophene-2-carboxylic acid

Yield: 76.0%

Dark brown solid $^1$H-NMR (400 MHz, CDCl$_3$) δ 8.87(bs, 1H), 7.81(dd, J=9.0, 8.7 Hz, 2H), 7.75(d, J=8.0 Hz, 1H), 7.61(bs, 1H), 7.50(d, J=5.5 Hz, 1H), 7.46(d, J=7.2 Hz, 1H), 7.40(dd, J=7.4, 7.0 Hz, 1H), 7.33(d, J=7.3 Hz, 1H), 7.21(d, J=5.3 Hz, 1H)

Compound No. 19: 3-((4-methoxy)-2-naphthylamino)thiophene-2-carboxylic acid

Yield: 60.0%

Brown solid $^1$H-NMR (400 MHz, CDCl$_3$) δ 8.86(bs, 1H), 8.18(d, J=8.3 Hz, 1H), 7.69(d, J=8.2 Hz, 1H), 7.51(d, J=5.5 Hz, 1H), 7.49-7.45(m, 1H), 7.40-7.36(m, 1H), 7.25(d, J=6.0 Hz, 1H), 7.23(d, J=1.3 Hz, 1H), 6.64(d, J=1.8 Hz, 1H)

Example 2

Preparation of nitro-3-(arylamino)thiophene-2-carboxylic acid

(2-1) Preparation of 3-bromo-nitrothiophene-2-carboxylic acid methylester

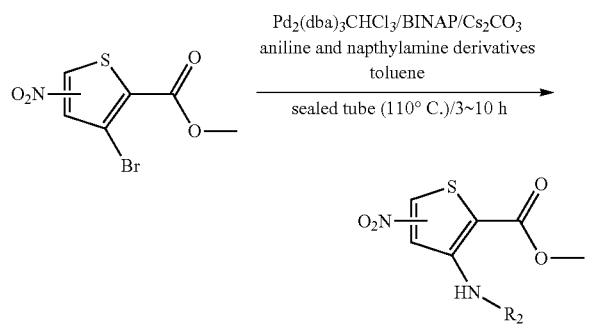

3-bromo-thiophene-2-carboxylic acid methylester reacted with sulfuric acid and sodium nitrate at 0° C., to prepare 3-bromo-nitrothiophene-2-carboxylic acid methylester having a thiophene ring substituted with a nitro group.

The compound prepared according to a representative synthetic method in Example 2-1 may include:

3-bromo-5-nitrothiophene-2-carboxylic acid methylester

Yield: 50.1%
White solid
$^1$H-NMR (400 MHz, CDCl$_3$) δ 7.86(s, 1H), 3.96(s, 3H)

3-bromo-4-nitrothiophene-2-carboxylic acid methylester

Yield: 20.7%
White solid
$^1$H-NMR (400 MHz, CDCl$_3$) δ 8.51(s, 1H), 3.97(s, 3H)

(2-2) Preparation of nitro-3-(arylamino)thiophene-2-carboxylic acid methylester

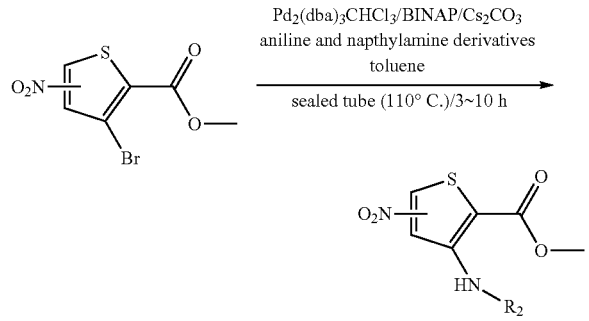

After dissolving 3-bromo-nitrothiophene-2-carboxylic acid methylester in a toluene solvent, a tris(dibenzylidineacetone)dipalladium.chloroform complex (Pd$_2$(dba)$_3$.CHCl$_3$) as a palladium catalyst, 2,2'-bis(diphenylphosphino)-1,1'-binaphthalene (BINAP) as a ligand, cesium carbonate (Cs$_2$CO$_3$) as a base, and a variety of amine derivatives represented by R$_2$NH$_2$ were added thereto, followed by heating and reacting the mixture at a temperature of 110, to prepare nitro-3-(arylamino)thiophene-2-carboxylic acid methylester.

(2-3) Preparation of nitro-3-(arylamino)thiophene-2-carboxylic acid

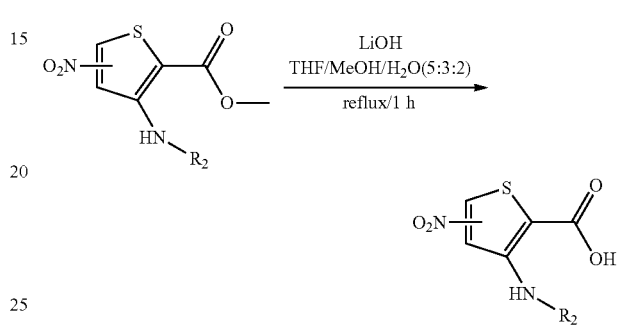

Nitro-3-(arylamino)thiophene-2-carboxylic acid methylester and LiOH were added to a mixed solvent including tetrahydrofuran:methanol:water in a ratio by volume of 5:3:2, followed by refluxing the mixture, to prepar nitro-3-(arylamino)thiophene-2-carboxylic acid.

The compound represented by formula 1 prepared according to a representative synthetic method in Example 2-3 may include:

Compound No. 20: 4-nitro-3-(4-chlorophenylamino)thiophene-2-carboxylic acid
Yield: 84.2%
Reddish brown solid
$^1$H-NMR (400 MHz, DMSO-d$_6$) δ 8.92(bs, 1H), 7.85(s, 1H), 7.40(d, J=8.8 Hz, 2H), 7.30(d, J=8.8 Hz, 2H)

Compound No. 21: 4-nitro-3-(4-bromophenylamino)thiophene-2-carboxylic acid
Yield: 92.5%
Reddish brown solid
$^1$H-NMR (400 MHz, DMSO-d$_6$) δ 8.93(bs, 1H), 7.87(s, 1H), 7.52(d, J=8.8 Hz, 2H), 7.25(d, J=8.8 Hz, 2H)

Compound No. 22: 4-nitro-3-(4-iodophenylamino)thiophene-2-carboxylic acid
Yield: 90.9%
Reddish brown solid
$^1$H-NMR (400 MHz, DMSO-d$_6$) δ 8.95(bs, 1H), 7.87(s, 1H), 7.67(d, J=8.4 Hz, 2H), 6.93(d, J=8.4 Hz, 2H)

Compound No. 23: 4-nitro-3-((4-methoxy)-2-naphthylamino)thiophene-2-carboxylic acid
Yield: 96.2%
Dark brown solid
$^1$H-NMR (400 MHz, DMSO-d$_6$) δ 9.02(bs, 1H), 8.05(d, J=4.9 Hz, 2H), 7.79(d, J=8.2 Hz, 1H), 7.48(dd, J=7.2, 7.2 Hz, 1H), 7.37(dd, J=7.4, 7.3 Hz, 1H), 7.32(s, 1H), 6.96(s, 1H), 3.98(s, 3H)

Compound No. 24: 5-nitro-3-(4-chlorophenylamino)thiophene-2-carboxylic acid
Yield: 32.2%
Yellow solid
$^1$H-NMR (400 MHz, DMSO-d$_6$) δ 9.00(s, 1H), 8.76(bs, 1H), 7.23(d, J=8.8 Hz, 2H), 6.92(d, J=8.8 Hz, 2H)

Compound No. 25: 5-nitro-3-(4-bromophenylamino)thiophene-2-carboxylic acid

Yield: 29.4%

Yellow solid $^1$H-NMR (400 MHz, DMSO-$d_6$) δ 9.00(s, 1H), 8.77(bs, 1H), 7.34(d, J=8.7 Hz, 2H), 6.85(d, J=8.7 Hz, 2H)

Example 3

Preparation of nitroanthranilic acid Derivatives

(3-1) Preparation of 2-bromo-nitrobenzoic acid methylester

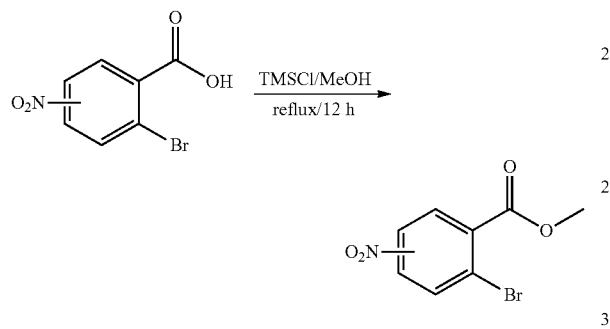

By refluxing 2-bromo-3-nitrobenzoic acid and trimethylsilyl chloride (TMSCl) in a methanol solvent for 12 hours, 2-bromo-nitrobenzoic acid methylester was prepared.

The compound prepared according to a representative synthetic method in Example 3-1 may include:

2-bromo-3-nitrobenzoic acid methylester

Yield: 95.4%

White solid $^1$H-NMR (400 MHz, CDCl$_3$) δ 7.85(dd, J=7.9, 1.6 Hz, 1H), 7.76(d, J=7.9, J=1.6 Hz, 1H), 7.52(dd, J=7.9, 7.9 Hz, 1H), 3.98(s, 3H)

2-bromo-4-nitrobenzoic acid methylester

Yield: 95.5%

Yellow solid $^1$H-NMR (400 MHz, CDCl$_3$) δ 8.52(d, J=2.2 Hz, 1H), 8.21(dd, J=8.5, 2.2 Hz, 1H), 7.92(d, J=8.5 Hz, 1H), 3.99(s, 3H)

(3-2) Preparation of N-aryl-nitroanthranilic acid methylester

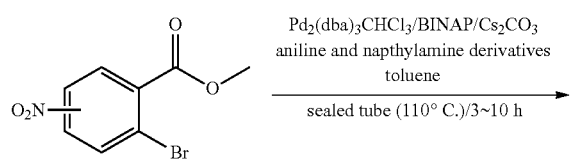

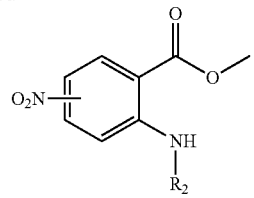

After dissolving 2-bromo-nitrobenzoic acid methylester in a toluene solvent, a tris(dibenzylidineacetone)dipalladium.chloroform complex (Pd$_2$(dba)$_3$.CHCl$_3$) as a palladium catalyst, 2,2'-bis(diphenylphosphino)-1,1'-binaphthalene (BINAP) as a ligand, cesium carbonate (Cs$_2$CO$_3$) as a base, and a variety of amine derivatives represented by R$_2$NH$_2$ were added thereto, followed by heating and reacting the mixture at a temperature of 110° C., to prepare N-aryl-nitroanthranilic acid methylester.

(3-3) Preparation of N-aryl-nitroanthranilic acid

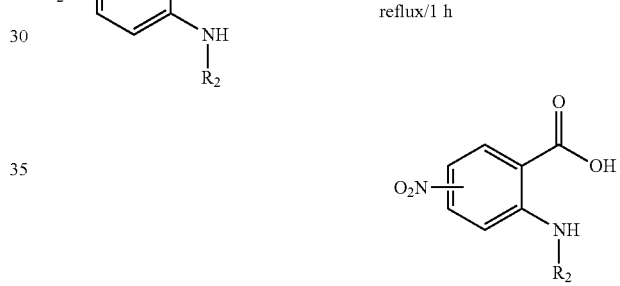

N-aryl-nitroanthranilic acid methylester and LiOH were added to a mixed solvent including tetrahydrofuran:methanol:water in a ratio by volume of 5:3:2, followed by refluxing the mixture, to prepare N-aryl-nitroanthranilic acid.

The compound represented by formula 1 prepared according to a representative synthetic method in Example 3-3 may include:

Compound No. 26: N-(4-fluorophenyl)-3-nitroanthranilic acid

Yield: 75.6%

Red solid $^1$H-NMR (400 MHz, DMSO-$d_6$) δ 9.93(bs, 1H), 8.19(d, J=7.5 Hz, 1H), 8.05(d, J=7.8 Hz, 1H), 7.08-7.06(m, 3H), 6.98(bs, 2H)

Compound No. 27: N-(4chlorophenyl)-3-nitroanthranilic acid

Yield: 87.5%

Yellow solid $^1$H-NMR (400 MHz, CDCl$_3$) δ 9.67(bs, 1H), 8.25(dd, J=7.8, 1.6 Hz, 1H), 8.10(dd, J=7.8, 1.6 Hz, 1H), 7.26-7.22 (m, 2H), 7.00(dd, J=8.0, 8.0 Hz, 1H), 6.95-6.91(m, 2H)

Compound No. 28: N-naphthyl-3-nitroanthranilic acid

Yield: 94.4%

Yellow solid $^1$H-NMR (400 MHz, DMSO-$d_6$) δ 10.42(bs, 1H), 8.28(d, J=6.9 Hz, 1H), 8.18(d, J=5.4 Hz, 1H), 8.07(d, J=6.6 Hz, 1H), 7.95(d, J=6.6 Hz, 1H), 7.63-7.61(m, 3H), 7.30(bs, 1H), 7.11(bs, 1H), 6.92(d, J=6.9 Hz, 1H)

Compound No. 29: N-((4-chloro)naphthyl)-3-nitroanthranilic acid

Yield: 69.1%

Red solid $^1$H-NMR (400 MHz, DMSO-$d_6$) δ 10.60(bs, 1H), 8.29(d, J=4.4 Hz, 2H), 8.20(d, J=7.9 Hz, 1H), 8.08(d, J=7.8 Hz, 1H), 7.78-7.74(m, 2H), 7.48(d, J=7.9 Hz, 1H), 7.15(dd, J=7.7, 7.6 Hz, 1H), 6.89(d, J=7.7 Hz, 1H)

Compound No. 30: N-(2-naphthyl)-3-nitroanthranilic acid

Yield: 83.6%

Yellow solid $^1$H-NMR (400 MHz, DMSO-$d_6$) δ 10.04(bs, 1H), 8.23(d, J=6.1 Hz, 1H), 8.12(d, J=6.9 Hz, 1H), 7.81(d, J=4.2 Hz, 2H), 7.68(d, J=7.22 Hz, 1H), 7.43-7.36(m, 2H), 7.29(bs, 1H), 7.22-7.15(m, 2H)

Compound No. 31: N-naphthyl-4-nitroanthranilic acid

Yield: 93.7%

Yellow solid $^1$H-NMR (400 MHz, DMSO-$d_6$) δ 10.20(bs, 1H), 8.17(d, J=8.7 Hz, 1H), 8.05(dd, J=7.9, 1.8 Hz, 1H), 7.96(d, J=7.4 Hz, 1H), 7.91(dd, J=8.1, 1.8 Hz, 1H), 7.65-7.56(m, 4H), 7.50(dd, J=8.7, 2.2 Hz, 1H), 7.44(d, J=2.2 Hz, 1H)

Compound No 32: N-((4-fluoro)nphthyl)-4-nitroanthranilic acid

Yield: 88.5%

Reddish brown solid $^1$H-NMR (400 MHz, DMSO-$d_6$) δ 10.01(bs, 1H), 8.15(bs, 2H), 7.96(d, J=5.4 Hz, 1H), 7.70(bs, 2H), 7.60(bs, 1H), 7.47(bs, 2H), 7.25(bs, 1H)

Compound No. 33: N-((4-chloro)naphthyl)-4-nitroanthranilic acid

Yield: 98.1%

Red solid $^1$H-NMR (400 MHz, DMSO-$d_6$) δ 10.20(bs, 1H), 8.28(d, J=8.3, 1H), 8.18(d, J=8.7 Hz, 1H), 8.05(d, J=8.4 Hz, 1H), 7.81-7.77(m, 2H), 7.73-7.69(m, 1H), 7.63(d, J=8.0 Hz, 1H), 7.53(dd, J=8.7, 2.2 Hz, 1H), 7.45(d, J=2.1, 1H)

Compound No. 34: N-((4-bromo)naphthyl)-4-nitroanthranilic acid

Yield: 94.5%

Red solid $^1$H-NMR (400 MHz, DMSO-$d_6$) δ 10.23(bs, 1H), 8.23(d, J=8.4, 1H), 8.18(d, J=8.8 Hz, 1H), 8.05(d, J=8.5 Hz, 1H), 7.97(d, J=7.9 Hz, 1H), 7.79(dd, J=8.2, 6.9 Hz, 1H), 7.70(dd, J=7.6, 7.5 Hz, 1H), 7.58(d, J=8.0 Hz, 1H), 7.53(dd, J=8.7, 1.8 Hz, 1H), 7.48(d, J=1.8 Hz, 1H)

Compound No. 35: N-((4-nitro)naphthyl)-4-nitroanthranilic acid

Yield: 56.5%

Brown solid $^1$H-NMR (400 MHz, DMSO-$d_6$) δ 10.85(bs, 1H), 8.67(d, J=8.6 Hz, 1H), 8.42(d, J=7.6 Hz, 1H), 8.32(d, J=8.3 Hz, 1H), 8.22(d, J=8.7 Hz, 1H), 8.12(s, 1H), 7.89(dd, J=8.0, 7.2 Hz, 1H), 7.80(d, J=7.8 Hz, 2H), 7.64(d, J=8.5 Hz, 1H)

Compound No. 36: N-((4-methoxy)naphthyl)-4-nitroanthranilic acid

Yield: 93.6%

Brown solid $^1$H-NMR (400 MHz, DMSO-$d_6$) δ 9.88(bs, 1H), 8.28-8.25(m, 1H), 8.15(d, J=8.7 Hz, 1H), 7.85-7.83(m, 1H), 7.61-7.58(m, 2H), 7.53(d, J=8.1 Hz, 1H), 7.43(dd, J=8.5, 2.3 Hz, 1H), 7.14(d, J=2.3 Hz, 1H), 7.08(d, J=8.2 Hz, 1H), 4.04(s, 3H)

Compound No. 37: N-(2-naphthyl)-4-nitroanthranilic acid

Yield: 95.9%

Brown solid $^1$H-NMR (400 MHz, DMSO-$d_6$) δ 10.00(bs, 1H), 8.15(d, J=8.7 Hz, 1H), 8.01(d, J=8.7 Hz, 1H), 7.95-7.86(m, 4H), 7.57-7.50(m, 3H), 7.47(dd, J=7.1, 6.9 Hz, 1H)

Compound No. 38: N-((1-methoxy)-2-naphthyl)-4-nitroanthranilic acid

Yield: 98.1%

Orange solid $^1$H-NMR (400 MHz, DMSO-$d_6$) δ 10.05(bs, 1H), 8.17(d, J=8.7 Hz, 1H), 8.07(d, J=8.3 Hz, 1H), 7.97(d, J=8.0 Hz, 1H), 7.81(d, J=8.8 Hz, 1H), 7.77(d, J=2.2 Hz, 1H), 7.67(d, J=8.8 Hz, 1H), 7.62-7.55(m, 2H), 7.80(ddd, J=7.5, 7.5, 1.2 Hz 1H), 3.82(s, 3H)

Compound No. 39: N-((4-methoxy)-2-naphthyl)-4-nitroanthranilic acid

Yield: 95.6%

Brown solid $^1$H-NMR (400 MHz, DMSO-$d_6$) δ 9.99(bs, 1H), 8.15(d, J=8.7 Hz, 1H), 8.10(d, J=8.2 Hz, 1H), 8.04(d, J=2.2 Hz, 1H), 7.80(d, J=8.2 Hz, 1H), 7.57-7.50(m, 2H), 7.45-7.41(m, 2H), 6.97(s, 1H), 3.98(s, 3H)

Compound No. 40: N-naphthyl-5-nitroanthranilic acid

Yield: 79.9%

Brown solid $^1$H-NMR (400 MHz, DMSO-$d_6$) δ 10.72(bs, 1H), 8.78(d, J=2.7 Hz, 1H), 8.10(dd, J=9.4, 2.6 Hz, 1H), 8.06(d, J=7.3 Hz, 1H), 7.96(dd, J=6.4, 2.4 Hz, 1H), 7.90(d, J=7.6 Hz, 1H), 7.65-7.57(m, 4H), 6.69(d, J=9.4 Hz, 1H)

Compound No. 41: N-((4-fluoro)naphthyl)-5-nitroanthranilic acid

Yield: 86.7%

Yellow solid $^1$H-NMR (400 MHz, DMSO-$d_6$) δ 10.51(bs, 1H), 8.77(s, 1H), 8.16(d, J=8.0, Hz, 1H), 8.07(d, J=9.4 Hz, 1H), 7.90(d, J=7.8 Hz, 1H), 7.75-7.67(m, 2H), 7.61(dd, J=7.0, 5.2 Hz, 1H), 7.47(dd, J=8.6, 8.6 Hz, 1H), 6.56(d, J=9.4 Hz, 1H)

Compound No. 42: N-((4-chloro)naphthyl)-5-nitroanthranilic acid

Yield: 61.7%

Yellow solid $^1$H-NMR (400 MHz, DMSO-$d_6$) δ 10.77(bs, 1H), 8.76(d, J=2.7 Hz, 1H), 8.28(d, J=8.4 Hz, 1H), 8.10(dd, J=9.4, 2.7 Hz, 1H), 7.96(d, J=8.2 Hz, 1H), 7.82-7.73(m, 2H), 7.71(dd, J=7.8, 7.2 Hz, 1H), 7.61(d, J=8.0 Hz, 1H), 6.70(d, J=9.4 Hz, 1H)

Compound No. 43: N-((4-bromo)naphthyl)-5-nitroanthranilic acid

Yield: 97.6%

Brown solid $^1$H-NMR (400 MHz, DMSO-$d_6$) δ 10.72(bs, 1H), 8.77(d, J=2.7 Hz, 1H), 8.24(d, J=8.4 Hz, 1H), 8.09(dd, J=9.4, 2.8 Hz, 1H), 8.00-7.97(m, 2H), 7.79(dd, J=7.7, 7.3 Hz, 1H), 7.70(dd, J=7.7, 7.2 Hz, 1H), 7.55(d, J=8.0 Hz, 1H), 6.72(d, J=9.4 Hz, 1H)

Compound No. 44: N-((4-iodo)naphthyl)-5-nitroanthranilic acid

Yield: 83.3%

Yellow solid $^1$H-NMR (400 MHz, DMSO-$d_6$) δ 10.70(bs, 1H), 8.76(s, 1H), 8.22(d, J=7.7 Hz, 1H), 8.09(dd, J=8.0, 7.7 Hz, 2H), 7.91(d, J=8.2 Hz, 1H), 7.74(dd, J=7.6, 6.9 Hz, 1H), 7.65(dd, J=7.3, 7.2 Hz, 1H), 7.39(d, J=7.7 Hz, 1H), 6.72(d, J=9.3 Hz, 1H)

Compound No. 45: N-((2-methoxy)naphthyl)-5-nitroanthranilic acid
Yield: 85.2%
Yellow solid
$^1$H-NMR (400 MHz, DMSO-$d_6$) δ 10.18(bs, 1H), 8.75(d, J=2.8 Hz, 1H), 8.06-8.02(m, 2H), 7.98(d, J=8.0 Hz, 1H), 7.68(d, J=8.4 Hz, 1H), 7.63(d, J=9.2 Hz, 1H), 7.51(dd, J=8.0, 6.8 Hz, 1H), 7.43(dd, J=7.6, 7.2 Hz, 1H), 6.21(d, J=9.6 Hz, 1H), 3.90(s, 3H)

Compound No. 46: N-((3-methoxy)naphthyl)-5-nitroanthranilic acid
Yield: 94.6%
Orange solid
$^1$H-NMR (400 MHz, DMSO-$d_6$) δ 10.64(bs, 1H), 8.97(d, J=2.7 Hz, 1H), 8.06(dd, J=9.4, 2.6 Hz, 1H), 7.84(d, J=8.7 Hz, 1H), 7.82(d, J=9.3 Hz, 1H), 7.53-7.49(m, 1H), 7.39-7.35(m, 1H), 7.19(d, J=1.9 Hz, 1H), 7.15(d, J=2.3 Hz, 1H), 6.82(d, J=9.5 Hz, 1H), 3.91(s, 3H)

Compound No. 47: N-((4-methoxy)naphthyl)-5-nitroanthranilic acid
Yield: 91.2%
Yellow solid
$^1$H-NMR (400 MHz, DMSO-$d_6$) δ 10.53(bs, 1H), 8.76(d, J=2.8 Hz, 1H), 8.27-8.25(m, 1H), 8.05(dd, J=9.4, 2.8 Hz, 1H), 7.80-7.77(m, 1H), 7.60-7.58(m, 2H), 7.51(d, J=8.1 Hz, 1H), 7.08(d, J=8.2 Hz, 1H), 6.48(d, J=9.5 Hz, 1H), 4.01(s, 3H)

Compound No. 48: N-((5-methoxy)naphthyl)-5-nitroanthranilic acid
Yield: 75.1%
Yellow solid
$^1$H-NMR (400 MHz, DMSO-$d_6$) δ 10.66(bs, 1H), 8.77(d, J=2.8 Hz, 1H), 8.18(d, J=8.0 Hz, 1H), 8.10(dd, J=9.4, 2.8 Hz, 1H), 7.64-7.57(m, 2H), 7.50(dd, J=8.4, 7.6 Hz, 1H), 7.44(d, J=8.5 Hz, 1H), 7.08(d, J=7.6 Hz, 1H), 6.67(d, J=9.4 Hz, 1H), 4.01(s, 3H)

Compound No. 49: N-((6-methoxy)naphthyl)-5-nitroanthranilic acid
Yield: 90.1%
Yellow solid
$^1$H-NMR (400 MHz, DMSO-$d_6$) δ 10.65(bs, 1H), 8.75(d, J=2.8 Hz, 1H), 8.09(dd, J=9.4, 2.8 Hz, 1H), 7.84(d, J=8.0 Hz, 1H), 7.78(d, J=9.2 Hz, 1H), 7.56(dd, J=7.8, 7.6 Hz, 1H), 7.46(s, 1H), 7.41(d, J=7.2 Hz, 1H), 7.22(dd, J=9.0, 2.4 Hz, 1H), 6.66(d, J=9.6 Hz, 1H), 3.90(s, 3H)

Compound No. 50: N-((7-methoxy)naphthyl)-5-nitroanthranilic acid
Yield: 86.1%
Yellow solid
$^1$H-NMR (400 MHz, DMSO-$d_6$) δ 10.67(bs, 1H), 8.77(d, J=2.8 Hz, 1H), 8.12(dd, J=9.4, 2.8 Hz, 1H), 7.97(d, J=9.0 Hz, 1H), 7.87(d, J=8.1 Hz, 1H), 7.57(d, J=7.2 Hz, 1H), 7.45(dd, J=7.8, 7.7 Hz, 1H), 7.27(dd, J=9.0, 2.4 Hz, 1H), 7.18(d, J=2.3 Hz, 1H), 6.74(d, J=9.4 Hz, 1H), 3.78(s, 3H)

Compound No. 51: N-((8-methoxy)naphthyl)-5-nitroanthranilic acid
Yield: 95.8%
Yellow solid
$^1$H-NMR (400 MHz, DMSO-$d_6$) δ 11.53(bs, 1H), 8.75(d, J=2.8 Hz, 1H), 8.13(dd, J=9.5, 2.8 Hz, 1H), 7.74(d, J=7.6 Hz, 1H), 7.57-7.52(m, 3H), 7.46(dd, J=8.0, 7.8 Hz, 1H), 7.29(d, J=9.5 Hz, 1H), 7.01(d, J=7.6 Hz, 1H), 3.87(s, 3H)

Compound No. 52: N-(2-naphthyl)-5-nitroanthranilic acid
Yield: 70.7%
Yellow solid
$^1$H-NMR (400 MHz, DMSO-$d_6$) δ 10.20(bs, 1H), 8.75(dd, J=2.8, 0.7 Hz, 1H), 8.20(dd, J=9.4, 2.7 Hz, 1H), 8.01(d, J=8.7 Hz, 1H), 7.95(d, J=7.7 Hz, 1H), 7.92-7.91(m, 2H), 7.57-7.49(m, 3H), 7.27(d, J=9.5 Hz, 1H)

Compound No. 53: N-((1-methoxy)-2-naphthyl)-5-nitroanthranilic acid
Yield: 96.8%
Yellow solid
$^1$H-NMR (400 MHz, DMSO-$d_6$) δ δ 10.62(bs, 1H), 8.77(d, J=2.8 Hz, 1H), 8.21(dd, J=9.4, 2.8 Hz, 1H), 8.10(d, J=8.2 Hz, 1H), 7.98(d, J=7.8 Hz, 1H), 7.81(d, J=8.7 Hz, 1H), 7.63-7.59(m, 2H), 7.57-7.55(m, 1H), 7.08(d, J=9.4 Hz, 1H), 3.83(s, 3H)

Compound No. 54: N-((3-methoxy)-2-naphthyl)-5-nitroanthranilic acid
Yield: 91.1%
Yellow solid
$^1$H-NMR (400 MHz, DMSO-$d_6$) δ 10.64(bs, 1H), 8.74(d, J=1.7 Hz, 1H), 8.21(d, J=7.6 Hz, 1H), 7.98(s, 1H), 7.84-7.81(m, 2H), 7.50(s, 1H), 7.46-7.36(m, 3H), 3.96(s, 3H)

Compound No. 55: N-((4-methoxy)-2-naphthyl)-5-nitroanthranilic acid
Yield: 98.0%
Orange solid
$^1$H-NMR (400 MHz, DMSO-$d_6$) δ 10.54(bs, 1H), 8.74(d, J=2.6 Hz, 1H), 8.19(dd, J=9.4, 2.5 Hz 1H), 8.11(d, J=8.2 Hz, 1H), 7.84(d, J=8.0 Hz, 1H), 7.56-7.45(m, 3H), 7.35(d, J=9.4 Hz, 1H), 6.95(d, J=9.5 Hz, 1H)

Compound No.56: N-((5-methoxy)-2-naphthyl)-5-nitroanthranilic acid
Yield: 95.6%
Yellow solid
$^1$H-NMR (400 MHz, DMSO-$d_6$) δ 10.58(bs, 1H), 8.74(d, J=2.8 Hz, 1H), 8.20(dd, J=8.9, 2.5 Hz, 1H), 7.86(d, J=1.9 Hz, 1H), 7.48-7.45(m, 3H), 7.28(d, J=9.4 Hz, 1H), 6.96(dd, J=4.4, 4.3 Hz, 1H), 3.98(s, 3H)

Compound No. 57: N-((6-methoxy)-2-naphthyl)-5-nitroanthranilic acid
Yield: 85.4%
Yellow solid
$^1$H-NMR (400 MHz, DMSO-$d_6$) δ 10.50(bs, 1H), 8.74(d, J=2.7 Hz, 1H), 8.17(dd, J=9.4, 2.6 Hz, 1H), 7.91(d, J=8.7 Hz, 1H), 7.84-7.81(m, 2H), 7.44(dd, J=8.7, 1.6 Hz, 1H), 7.37(d, J=1.8 Hz, 1H), 7.20(dd, J=8.9, J=2.2 Hz, 1H), 7.16(d, J=9.4 Hz, 1H), 3.89(s, 3H)

Compound No. 58: N-((7-methoxy)-2-naphthyl)-5-nitroanthranilci acid
Yield: 94.9%
Yellow solid
$^1$H-NMR (400 MHz, DMSO-$d_6$) δ 10.55(bs, 1H), 8.73(d, J=2.8 Hz, 1H), 8.19(dd, J=9.4, 2.8 Hz, 1H), 7.91(d, J=8.6 Hz, 1H), 7.83(d, J=9.0 Hz, 1H), 7.78(d, J=1.3 Hz, 1H), 7.32-7.29(m, 2H), 7.28(d, J=9.4 Hz, 1H), 7.14(dd, J=8.9, 2.4 Hz, 1H), 3.87(s, 3H)

Compound No. 59: N-((8-methoxy)-2-naphthyl)-5-nitroanthranilic acid
Yield: 91.1%
Yellow solid
$^1$H-NMR (400 MHz, DMSO-$d_6$) 10.56(bs, 1H), 8.74(d, J=2.6 Hz, 1H), 8.20(dd, J=9.4, 2.6 Hz, 1H), 8.03(s, 1H), 7.98(d, J=8.6 Hz, 1H), 7.51(d, J=8.5 Hz, 1H), 7.43(dd, J=7.7, 7.7 Hz, 1H), 7.22(d, J=9.4 Hz, 1H), 7.01(d, J=7.5 Hz, 1H), 3.97(s, 3H)

Compound No. 60: N-((7-bromo)-2-naphthyl)-5-nitroanthranilic acid
Yield: 85%
Yellow solid
$^1$H-NMR (400 MHz, DMSO-$d_6$) δ 10.64(bs, 1H), 8.73(d, J=2.7, Hz, 1H), 8.20-8.17(m, 2H), 8.01(d, J=8.6 Hz, 1H), 7.89(d, J=8.2 Hz, 2H), 7.60-7.58(m, 1H), 7.53(dd, J=8.6, 1.8 Hz, 1H), 7.33(d, J=9.4 Hz, 1H)

Compound No. 61: N-((7-iodo)-2-naphthyl)-5-nitroanthranilic acid
Yield: 96.2%
Yellow solid
$^1$H-NMR (400 MHz, DMSO-$d_6$) δ 10.93(bs, 1H), 8.75(bs, 1H), 8.37(bs, 1H), 8.18(d, J=6.7 Hz, 1H), 7.99(d, J=8.5 Hz, 1H), 7.86(bs, 1H), 7.74(bs, 2H), 7.51(d, J=8.0 Hz, 1H), 7.34(d, J=8.6 Hz, 1H)

Compound No. 62: N-((4-bromo)-2-naphthyl)-5-nitroanthranilic acid
Yield: 93.5%
Yellow solid
$^1$H-NMR (400 MHz, DMSO-$d_6$) δ 10.51(bs, 1H), 8.74 (s, 1H), 8.22(d, J=9.8 Hz, 1H), 8.11(d, J=8.0 Hz, 1H), 8.00-7.93(m, 3H), 7.66-7.64(m, 2H), 7.30(d, J=8.8 Hz, 1H)

Compound No. 63: N-((4-iodo)-2-naphthyl)-5-nitroanthranilic acid
Yield: 95.3%
Yellow solid
$^1$H-NMR (400 MHz, DMSO-$d_6$) δ 10.53(bs, 1H), 8.74(bs, 1H), 8.21(d, J=8.0 Hz, 1H), 8.13(bs, 1H), 8.00(bs, 2H), 7.91(d, J=5.9 Hz, 1H), 7.62(bs, 2H), 7.28(d, J=8.8 Hz, 1H)

Compound No. 64: N-((8-bromo)-2-naphthyl)-5-nitroanthranilic acid
Yield: 92.4%
Yellow solid
$^1$H-NMR (400 MHz, DMSO-$d_6$) δ 10.69(bs, 1H), 8.75(d, J=2.8 Hz, 1H), 8.22(dd, J=9.4, 2.8 Hz, 1H), 8.09(d, J=8.8 Hz, 1H), 8.03 (s, 1H), 8.00(d, J=8.2 Hz, 1H), 7.90(d, J=7.4 Hz, 1H), 7.62(dd, J=8.7, 1.9 Hz, 1H), 7.42(d, J=7.8, 7.8 Hz, 1H), 7.33(d, J=9.4 Hz, 1H)

Example 4

Preparation of trifluoromethylanthranilic acid Derivatives (4-1) Preparation of 2-hydroxy-4-trifluoromethylbenzoic acid methylester

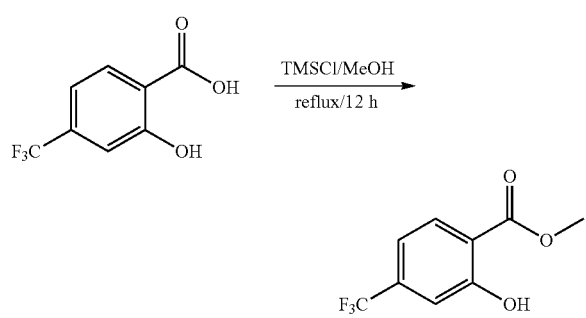

By refluxing 2-hydroxy-4-trifluoromethylbenzoic acid and trimethylsilyl chloride (TMSCl) in a toluene solvent for 12 hours, 2-hydroxy-4-trifluoromethylbenzoic acid methylester was prepared.

Yield: 89.1%
Red liquid
$^1$H-NMR (400 MHz, CDCl$_3$) δ 10.88(bs, 1H), 7.95(d, J=8.3 Hz, 1H), 7.25(s, 1H), 7.12(dd, J=8.3, 1.1 Hz, 1H), 3.99(s, 3H)

(4-2) Preparation of 2-trifluoromethylsulfonyloxy-4-trifluoromethylbenzoic acid methylester

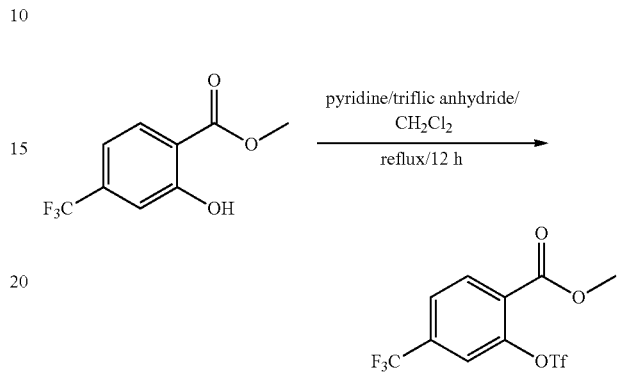

2-hydroxy-4-trifluoromethylbenzoic acid methylester, a pyridine base and trifluoromethane sulfonic acid (TfOH) anhydride were placed in a dichloromethane solvent and refluxed to prepare 2-trifluoromethylsulfonyloxy-4-trifluoromethylbenzoic acid methylester.

Yield: 95.7%
Yellow liquid
$^1$H-NMR (400 MHz, CDCl$_3$) δ 7.23(d, J=8.1 Hz, 1H), 7.75(dd, J=8.1, 0.8 Hz, 1H), 7.55(s, 1H), 4.01(s, 3H)

(4-3) Preparation of N-aryl-4-trifluoromethylanthranilic acid methylester

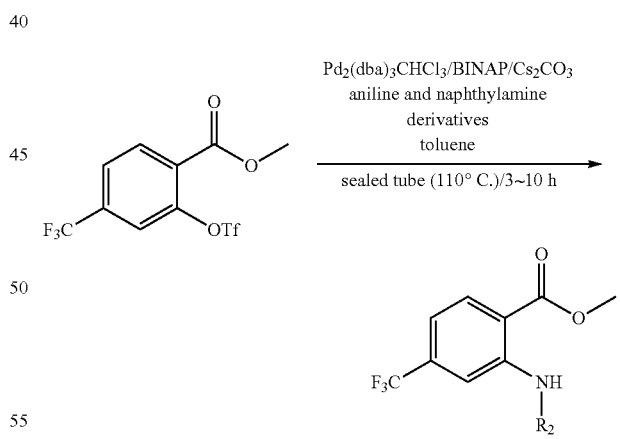

After dissolving 2-trifluoromethylsulfonyloxy-4-trifluoromethylbenzoic acid methylester in a toluene solvent, a tris(dibenzylidineacetone)dipalladium.chloroform complex (Pd$_2$(dba)$_3$.CHCl$_3$) as a palladium catalyst, 2,2'-bis(diphenylphosphino)-1,1'-binaphthalene (BINAP) as a ligand, cesium carbonate (Cs$_2$CO$_3$) as a base, and a variety of amine derivatives represented by R$_2$NH$_2$ were added thereto, followed by heating and reacting the mixture at a temperature of 110° C., to prepare N-aryl-4-trifluoromethylanthranilic acid methylester.

(4-4) Preparation of N-aryl-4-trifluoromethylanthranilic acid

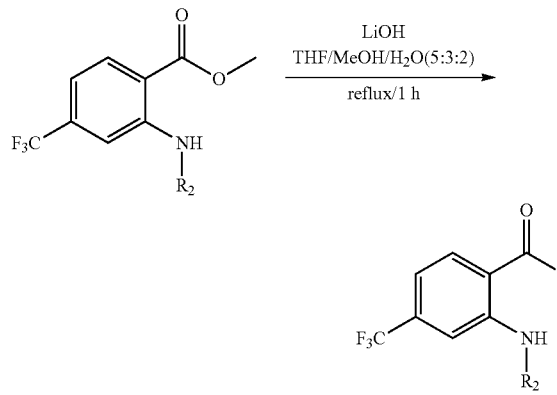

N-aryl-4-trifluoromethylanthranlic acid methylester and LiOH were added to a mixed solvent including tetrahydrofuran:methanol:water in a ratio by volume of 5:3:2, followed by refluxing the mixture, to prepare N-aryl-4-trifluoromethylanthranilic acid.

The compound represented by formula 1 prepared according to a representative synthetic method in Example 4-4 may include:

Compound No. 65: N-naphthyl-4-trifluoromethylanthranilic acid

Yield: 64.2%

White solid $^1$H-NMR (400 MHz, DMSO-d$_6$) δ 10.15(bs, 1H), 8.15(d, J=8.2 Hz, 1H), 8.03(d, J=8.2 Hz, 1H), 7.95(d, J=7.3 Hz, 1H), 7.89-7.87(m, 1H), 7.62-7.56(m, 4H), 7.05(d, J=8.2 Hz, 1H), 6.96(s, 1H)

Compound No. 66: N-((4-chloro)naphthyl)-4-trifluoromethylanthranilic acid

Yield: 98.3%

Yellow solid $^1$H-NMR (400 MHz, DMSO-d$_6$) δ 10.18(bs, 1H), 8.26(d, J=8.3 Hz, 1H), 8.15(d, J=8.2 Hz, 1H), 8.05(d, J=8.3 Hz, 1H), 7.80-7.76(m, 2H), 7.72-7.69(m, 1H), 7.58(d, J=8.0 Hz, 1H), 7.08(d, J=8.2 Hz, 1H), 6.99(bs, 1H), 3.98(s, 3H)

Compound No. 67: N-((4-nitro)naphthyl)-4-trifluoromethylanthranilic acid

Yield: 98.6%

Yellow solid $^1$H-NMR (400 MHz, DMSO-d$_6$) δ 10.74(bs, 1H), 8.69(d, J=8.8, 1H), 8.42(d, J=8.4 Hz, 1H), 8.33(d, J=8.2 Hz, 1H), 8.20(d, J=8.0 Hz, 1H), 7.90-7.87(m, 1H), 7.80-7.78(m, 1H), 7.72(s, 1H), 7.51(d, J=8.4 Hz, 1H), 7.39(d, J=7.8 Hz, 1H)

Compound No. 68: N-(2-naphthyl)-4-trifluoromethylanthranilic acid

Yield: 96.1%

Yellow solid $^1$H-NMR (400 MHz, DMSO-d$_6$) δ 9.97(bs, 1H), 8.12(d, J=8.3 Hz, 1H), 7.97(d, J=8.8 Hz, 1H), 7.90(d, J=8.0 Hz, 1H), 7.86(d, J=8.2 Hz, 1H), 7.80(bs, 1H), 7.53-7.44(m, 4H), 7.10(d, J=8.3 Hz, 1H)

Example 5

Preparation of nitroanthranilic acid Derivatives

(5-1) Preparation of 2-amino-6-nitrobenzoic acid methylester

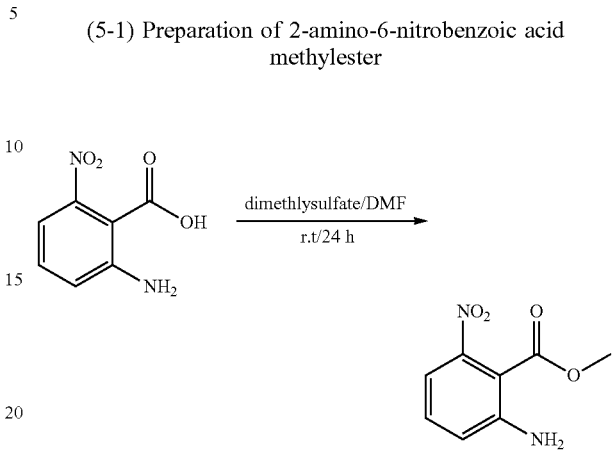

After dissolving 2-amino-6-nitrobenzoic acid, dimethylsulfate and a triethylamine base in a dimethylformamide solvent, the mixture was agitated at room temperature for 24 hours to prepare 2-amino-6-nitrobenzoic acid methylester.

Yield: 47.6%

Yellow solid $^1$H-NMR (400 MHz, CDCl3) δ 7.27(dd, J=8.2, 8.0 Hz, 1H), 7.02(dd, J=7.8, 0.9 Hz, 1H), 6.86(dd, J=8.4, 0.9 Hz, 1H), 5.31(bs, 2H), 3.83(s, 3H)

(5-2) Preparation of 2-iodo-6-nitroanthranilic acid methylester

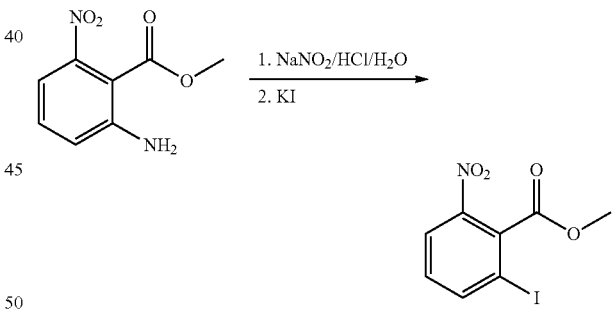

After dissolving 2-amino-6-nitrobenzoic acid methylester in a mixed solution including hydrochloric acid and water, a sodium nitrite (NaNO$_2$) solution was slowly added to the mixture at 0° C., followed by agitating for 2 hours, to prepare a diazonium solution. After preparing a potassium iodide (KI) solution in an alternative reactor, it was heated to 60° C. The prepared diazonium solution was slowly added to the potassium iodide (KI) solution, followed by heating and agitating the mixture for 1 hour, to prepare 2-iodo-6-nitrobenzoic acid methylester.

Yield: 82.8%,

Yellow solid $^1$H-NMR (400 MHz, CDCl3) δ 8.19(dd, J=8.3, 1.0 Hz, 1H), 8.16(dd, J=8.0, 1.0 Hz, 1H), 7.31(dd, J=8.1, 8.1 Hz, 1H), 4.03(s, 3H)

(5-3) Preparation of N-aryl-6-nitrobenzoic acid methylester

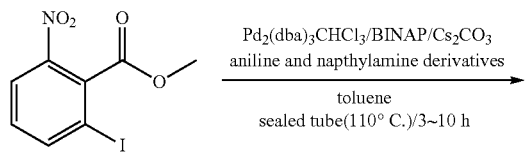

After dissolving 2-iodo-6-nitrobenzoic acid methylester in a toluene solvent, a tris(dibenzylideneacetone)dipalladium·chloroform complex (Pd$_2$(dba)$_3$·CHCl$_3$) as a palladium catalyst, 2,2'-bis(diphenylphosphino)-1,1'-binaphthalene (BINAP) as a ligand, cesium carbonate (Cs$_2$CO$_3$) as a base, and a variety of amine derivatives represented by R$_2$NH$_2$ were added thereto, followed by heating and reacting the mixture at a temperature of 110° C., to prepare N-aryl-6-nitrobenzoic acid methylester.

(5-4) Preparation of N-aryl-6-nitroanthranilic acid

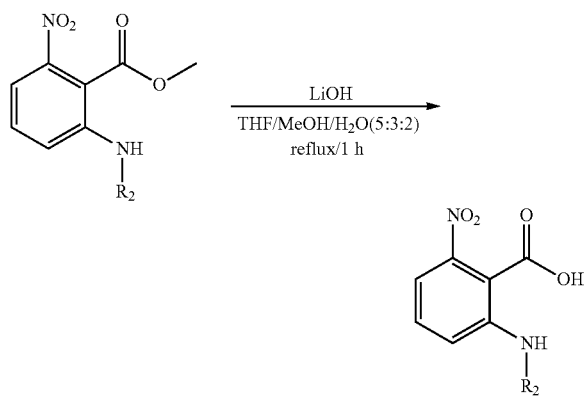

N-aryl-nitroanthranilic acid methylester and LiOH were added to a mixed solvent including tetrahydrofuran:methanol:water in a ratio by volume of 5:3:2, followed by refluxing the mixture, to prepare N-aryl-nitroanthranilic acid The compound prepared according to a representative synthetic method in Example 5-4 may include:

Compound No. 69: N-(4-bromophenyl-6-nitrobenzoic acid
Yield: 58.6%
Yellow solid
$^1$H-NMR (400 MHz, DMSO-d$_6$) δ 8.36(bs, 1H), 7.49-7.42(m, 5H), 7.09-7.07(m, 2H);

Compound No. 70: N-((4-bromo)naphthyl)-6-nitroanthranilic acid
Yield: 93.1%
Yellow solid
$^1$H-NMR (400 MHz, DMSO-d$_6$) δ 8.79(bs, 1H), 8.18(d, J=8.3 Hz, 1H), 8.02(d, J=8.0, Hz, 1H), 7.86(d, J=7.8 Hz, 1H), 7.25-7.65(m, 2H), 7.39(dd, J=8.0, 7.9 Hz, 1H), 7.32-7.28(m, 2H), 6.96(d, J=8.4 Hz, 1H)

Example 6

Preparation of nitroanthranilic acid Derivatives

(6-1) Preparation of 5-nitroanthranilic acid methylester

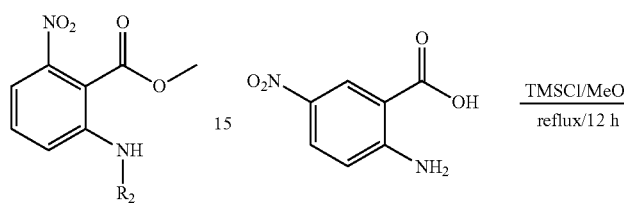

By refluxing 5-nitroanthranilic acid and trimethylsilyl chloride (TMSCl) in a methanol solvent for 12 hours, 2-bromo-nitrobenzoic acid methylester was prepared.
Yield: 93.2%
White solid
$^1$H-NMR (400 MHz, CDCl3) δ 8.00(d, J=8.8 Hz, 1H), 7.50(d, J=2.2 Hz, 1H), 7.40(dd, J=8.8, 2.2 Hz, 1H)

(6-2) Preparation of N-alkylaryl-nitroanthranilic acid methylester

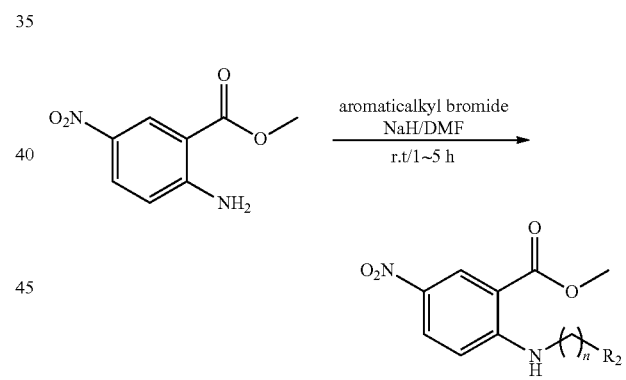

After dissolving 5-nitroanthranilic acid methylester in a dimethylformamide solvent, sodium iodide was slowly added thereto then agitated for 30 minutes. After adding aromatic alkyl bromide, a reaction was conducted for 1 to 5 hours to prepare N-alkyaryl-nitroanthranilic acid methylester.

(6-3) Preparation of N-alkyl-nitroanthranilic acid

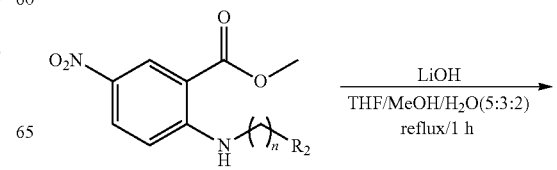

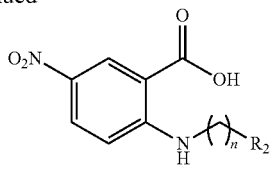

N-alkylaryl-nitroanthranilic acid methylester and LiOH were added to a mixed solvent including tetrahydrofuran:methanol:water in a ratio by volume of 5:3:2, followed by refluxing the mixture, to prepare N-alkylaryl-nitroanthranilic acid.

The compound prepared according to a representative synthetic method in Example 6-3 may include:

Compound No. 71: 2-(benzylamino)-5-nitroanthranilic acid
Yield: 94.3%
Yellow solid
$^1$H-NMR (400 MHz, DMSO-$d_6$) δ 9.20(bs, 1H), 8.66(d, J=2.6 Hz, 1H), 8.15-8.12(m, 1H), 7.37-7.29(m, 5H), 6.84(d, J=9.4 Hz, 1H), 4.64(d, J=5.8 Hz, 2H)

Compound No. 72: 2-(phenylbutylamino)-5-nitroanthranilic acid
Yield: 92.4%
Yellow solid
$^1$H-NMR (400 MHz, DMSO-$d_6$) δ 8.84(bs, 1H), 8.63(m, 1H), 8.15(d, J=8.9 Hz, 1H), 7.29-7.16(m, 5H), 6.88(d, J=9.2 Hz, 1H), 2.64-2.50(m, 4H), 1.70-1.60(m, 4H)

Compound No. 73: 2-(2-naphthylmethylamino)-5-nitroanthranilic acid
Yield: 95.6%
Yellow solid
$^1$H-NMR (400 MHz, DMSO-$d_6$) δ 9.35(bs, 1H), 8.68 (s, 1H), 8.12(d, J=9.2 Hz, 1H), 7.93-7.85(m, 4H), 7.52-7.50(m, 3H), 6.88(d, J=9.4 Hz, 1H), 4.81(d, J=5.4 Hz, 2H)

Example 7

Preparation of nitroanthranilic acid Derivatives (7-1) Preparation of 2-chloro-5-nitrobenzoic acid methylester

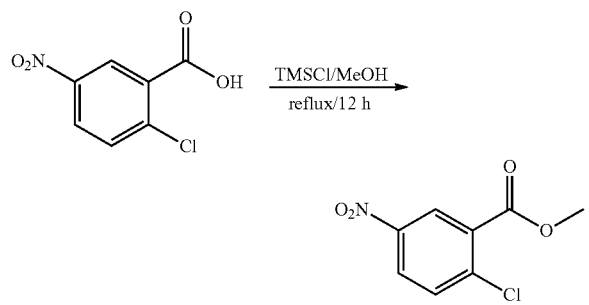

By refluxing 2-chloro-5-nitrobenzoic acid and trimethylsilyl chloride (TMSCl) in a methanol solvent for 12 hours, 2-bromo-nitrobenzoic acid methylester was prepared.
Yield: 92.5%
White solid
$^1$H-NMR (400 MHz, CDCl3) δ 8.72(d, J=2.6 Hz, 1H), 7.28(dd, J=8.8, 2.7 Hz, 1H), 7.66(d, J=8.8 Hz, 1H)

(7-2) Preparation of N-alkylaryl-nitroanthranilic acid methylester

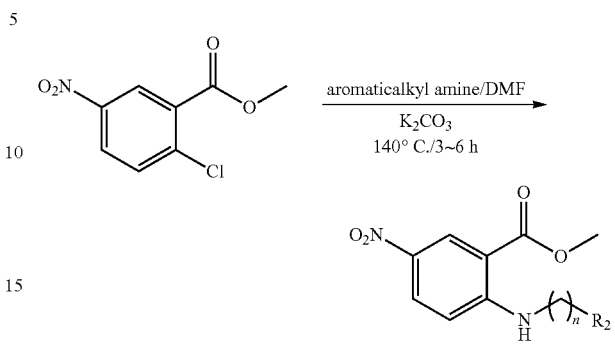

After dissolving 2-chloro-5-nitrobenzoic acid methylester and potassium carbonate in a dimethylformamide solvent, a reaction was conducted at 140° C. for 3 to 6 hours to prepare N-alkylaryl-nitroanthranilic acid methylester.

(7-3) Preparation of N-alkyl-nitroanthranilic acid

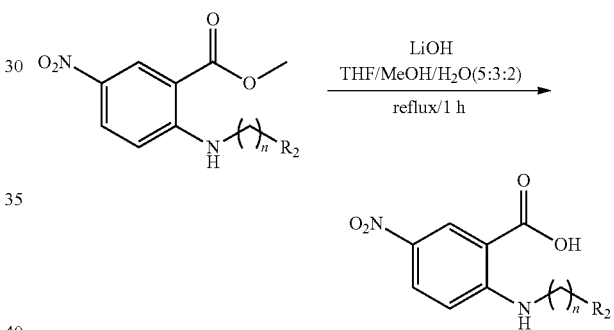

N-alkylaryl-nitroanthranilic acid methylester and LiOH were added to a mixed solvent including tetrahydrofuran:methanol:water in a ratio by volume of 5:3:2, followed by refluxing the mixture, to prepare N-alkylaryl-nitroanthranilic acid.

The compound prepared according to a representative synthetic method in Example 7-3 may include:

Compound No. 74: 2-(2-naphthylethylamio)-5-nitroanthranilic acid
Yield: 96%
Yellow solid
$^1$H-NMR (400 MHz, DMSO-$d_6$) δ 8.85(bs, 1H), 8.61(d, J=2.6 Hz, 1H), 8.19-8.16(m, 1H), 7.88-7.81(m, 4H), 7.50-7.46(m, 3H), 7.01(d, J=9.5 Hz, 1H), 3.72-3.69(m, 2H), 3.12-3.09(m, 2H)

Compound No. 75: 2-(phenylethylamino)-5-nitroanthranilic acid
$^1$H-NMR (400 MHz, DMSO-$d_6$) δ 8.82(bs, 1H), 8.62(d, J=2.4 Hz, 1H), 8.17(d, J=9.4 Hz, 1H), 7.31-7.21(m, 5H), 6.96(d, J=9.5 Hz, 1H), 3.62-3.57(m, 2H), 2.95-2.91(m, 2H)

Meanwhile, the novel compound represented by formula 1 according to the present invention may be formulated in various forms depending upon purposes thereof. Hereinafter, with regard to manufacturing a formulation that contains the compound represented by formula 1 according to the present invention as an active ingredient, preferred embodiments will be illustrated, however, the present invention is not particularly limited thereto.

Preparative Example

Formulation 1: Tablet (Direct Pressing)

5.0 mg of an active ingredient, after sieving, was mixed with 14.1 mg of lactose, 0.8 mg of crospovidone USNF and 0.1 mg of magnesium stearate and pressed, to form tablets.

Formulation 2: Tablet (Wet Granulation)

5.0 mg of an active ingredient, after sieving, was mixed with 16.0 mg of lactose and 4.0 mg of starch. After dissolving 0.3 mg of polysorbate 80 in pure water, this solution was added in a predetermined amount to the above mixture, followed by atomization. After drying and sieving the same to prepare fine particles, it was mixed with 2.7 mg of colloidal silicon dioxide and 2.0 mg of magnesium stearate. The obtained fine particles were pressed to form tablets.

Formulation 3: Powder and Capsule 5.0 mg of an active ingredient, after sieving, was mixed with 14.8 mg of lactose, 10.0 mg of polyvinyl pyrrolidone and 0.2 mg of magnesium stearate. A hard galatin capsule No. 5 was filled with this mixture by means of any proper device.

Formula 4: Injection 100 mg of active ingredient, 180 mg of mannitol, 26 mg of $Na_2HPO_4.12H_2O$ and 2974 mg of distilled water were admixed to prepare an injection.

Meanwhile, with regard to the novel compound represented by formula 1 according to the present invention, calcium-dependent chloride channel blocking activity was assessed by a patch clamp method according to the following experimental examples.

Experimental Example

Experimental Example 1: Patch Clamp Method

Eggs of African *Xenopus laevis* were collected through surgical operation, immersed in a Barth's solution [88 mM NaCl, 1 mM KCl, 2.4 mM $NaHCO_3$, 10 mM HEPES, 0.82 mM $MgSO_4$, 0.33 mM $Ca(NO_3)_2$, 0.91 mM $CaCl_2$ (all of which were purchased from Sigma Co.); 10 units/mL peniciline, and streptomycin (purchased from Gibco Co.)], and cultured in an incubator at a constant temperature of 18° C. Such prepared eggs were treated using 10 μM ionomycin (Sigma) for 30 minutes. A recording solution (96 mM NaCl, 2 mM KCl, 10 mM HEPES, 3 mM NaOH, 2 mM $MgCl_2$, 0.5 mM EGTA, Sigma) was prepared and the eggs treated with ionomycin were rinsed using the prepared recording solution. Further, the eggs, after treating with 1 μM thapsigargin (Sigma) for 2 hours, were rinsed again using the recording solution to prepare eggs for recording. Next, an intracellular solution was prepared by adding 0.5 mM EGTA and 1 μM chelerythrine (Sigma) to 1 M KCl solution, then, charged in a glass micro-electrode. One of the prepared eggs was placed on a chamber and two micro-electrodes were stuck into both sides of the egg while dripping the recording solution over the egg. According to a protocol corresponding to purposes for experiments, two-electrode voltage clamp recording was executed to measure an electrical current.

$IC_{50}$ values of the novel compound according to the present invention, in terms of calcium ion-activated chloride channel, were obtained by the foregoing experiment and shown in Table 1 below.

TABLE 1

| Name of compound | $IC_{50}$ (μM) | N |
|---|---|---|
| 3-(4-fluorophenylamino)thiophene-2-carboxylic acid | 35.4 | 5 |
| 3-(4-chlorophenylamino)thiophene-2-carboxylic acid | 4.94 | 9 |
| 3-(4-bromophenylamino)thiophene-2-carboxylic acid | 5.63 | 14 |
| 3-(4-(trifluoromethyl)phenylamino)thiophene-2-carboxylic acid | 5.53 | 11 |
| 3-(4-methylphenylamino)thiophene-2-carboxylic acid | 61.5 | 5 |
| 3-(4-methoxyphenylamino)thiophene-2-carboxylic acid | 139.6 | 8 |
| 3-(2-(trifluoromethyl)phenylamino)thiophene-2-carboxylic acid | 82.6 | 5 |
| 3-(2,4-bis(trifluoromethyl)phenylamino)thiophene-2-carboxylic acid | 51.6 | 5 |
| 3-(2,4-difluorophenylamino)thiophene-2-carboxylic acid | 33.4 | 6 |
| 3-(2,6-difluorophenylamino)thiophene-2-carboxylic acid | no blocking | |
| 3-(3,5-dichlorophenylamino)thiophene-2-carboxylic acid | 13.4 | 6 |
| 3-(3-fluoro-4-methoxyphenylamino)thiophene-2-carboxylic acid | 105.3 | 5 |
| 3-(1-naphthylamino)thiophene-2-carboxylic acid | 15.2 | 6 |
| 3-((4-methoxy)-2-naphthylamino)thiophene-2-carboxylic acid | 4.55 | 7 |
| 3-(2-naphthylamino)thiophene-2-carboxylic acid | 8.2 | 6 |
| 3-((4-nitro)-1-naphthylamino)thiophene-2-carboxylic acid | 10.2 | 7 |
| 3-((4-chloro)-1-naphthylamino)thiophene-2-carboxylic acid | 9.7 | 6 |
| 3-((5-methoxy)-1-naphthylamino)thiophene-2-carboxylic acid | 15.7 | 6 |
| 3-((4-methoxy)-1-naphthylamino)thiophene-2-carboxylic acid | 10.7 | 6 |
| 4-nitro-3-(4-chlorophenylamino)thiophene-2-carboxylic acid | 3.7 | 8 |
| 4-nitro-3-(4-bromophenylamino)thiophene-2-carboxylic acid | 2.2 | 6 |
| 4-nitro-3-(4-iodophenylamino)thiophene-2-carboxylic acid | 4.1 | 8 |
| 4-nitro-3-((4-methoxy)-2-naphthylamino)thiophene-2-carboxylic acid | 2.5 | 8 |
| 5-nitro-3-(4-chlorophenylamino)thiophene-2-carboxylic acid | 13.4 | 7 |
| 5-nitro-3-(4-bromophenylamino)thiophene-2-carboxylic acid | 7.6 | 7 |
| N-naphthyl-5-nitroanthranilic acid | 5 | 6 |
| N-((4-fluoro)naphthyl)-5-nitroanthranilic acid | 3 | 4 |
| N-((4-chloro)naphthyl)-5-nitroanthranilic acid | 8 | 6 |
| N-((4-bromo)naphthyl)-5-nitroanthranilic acid | 1.5 | 7 |
| N-((4-iodo)naphthyl)-5-nitroanthranilic acid | 1.2 | 7 |
| N-((2-methoxy)naphthyl)-5-nitroanthranilic acid | 9.1 | 6 |
| N-((3-methoxy)naphthyl)-5-nitroanthranilic acid | 1.8 | 7 |
| N-((4-methoxy)naphthyl)-5-nitroanthranilic acid | 2.27 | 6 |
| N-((5-methoxy)naphthyl)-5-nitroanthranilic acid | 9.2 | 6 |
| N-((6-methoxy)naphthyl)-5-nitroanthranilic acid | 1.14 | 5 |
| N-((7-methoxy)naphthyl)-5-nitroanthranilic acid | 3.4 | 8 |
| N-((8-methoxy)naphthyl)-5-nitroanthranilic acid | 8.6 | 8 |
| N-(2-naphthyl)-5-nitroanthranilic acid | 3.4 | 6 |
| N-((1-methoxy)-2-naphthyl)-5-nitroanthranilic acid | 10.1 | 6 |
| N-((3-methoxy)-2-naphthyl)-5-nitroanthranilic acid | no blocking | |
| N-((4-methoxy)-2-naphthyl)-5-nitroanthranilic acid | 0.038 | 12 |
| N-((5-methoxy)-2-naphthyl)-5-nitroanthranilic acid | 18.4 | 4 |
| N-((6-methoxy)-2-naphthyl)-5-nitroanthranilic acid | 6.7 | 5 |
| N-((7-methoxy)-2-naphthyl)-5-nitroanthranilic acid | 1.5 | 4 |
| N-((8-methoxy)-2-naphthyl)-5-nitroanthranilic acid | 1.3 | 6 |
| N-naphthyl-4-nitroanthranilic acid | 8.5 | 5 |
| N-((4-fluoro)naphthyl)-4-nitroanthranilic acid | 13.6 | 8 |
| N-((4-chloro)naphthyl)-4-nitroanthranilic acid | 4.8 | 5 |
| N-((4-bromo)naphthyl)-4-nitroanthranilic acid | 10.1 | 4 |
| N-((4-nitro)naphthyl)-4-nitroanthranilic acid | 21.6 | 7 |
| N-((4-methoxy)naphthyl)-4-nitroanthranilic acid | 15.2 | 4 |
| N-(2-naphthyl)-4-nitroanthranilic acid | 5.3 | 4 |
| N-((1-methoxy)-2-naphthyl)-4-nitroanthranilic acid | 17.5 | 6 |
| N-((4-methoxy)-2-naphthyl)-4-nitroanthranilic acid | 2.8 | 8 |
| N-naphthyl-3-nitroanthranilic acid | 54 | 5 |
| N-(2-naphthyl)-3-nitroanthranilic acid | 5.7 | 6 |
| N-((4-chloro)naphthyl)-3-nitroanthranilic acid | 16.6 | 5 |
| N-naphthyl-4-trifluoromethylanthranilic acid | 54 | 5 |
| N-((4-chloro)naphthyl)-4-trifluoromethylanthranilic acid | 5.7 | 5 |
| N-(2-naphthyl)-3-trifluoromethylanthranilic acid | 41.1 | 6 |
| N-((7-bromo)-2-naphthyl)-5-nitroanthranilic acid | 0.22 | 4 |
| N-((7-iodo)-2-naphthyl)-5-nitroanthranilic acid | 0.55 | 8 |

TABLE 1-continued

| Name of compound | IC$_{50}$ (μM) | N |
|---|---|---|
| N-((4-bromo)-2-naphthyl)-5-nitroanthranilic acid | 1.6 | 6 |
| N-((4-iodo)-2-naphthyl)-5-nitroanthranilic acid | 0.9 | 8 |
| N-((8-bromo)-2-naphthyl)-5-nitroanthranilic acid | 1.6 | 8 |
| N-(4-bromophenyl)-6-nitrobenzoic acid | 33.2 | 4 |
| N-((4-bromo)naphthyl)-6-nitroanthranilic acid | 8.6 | 7 |
| 2-(benzylamino)-5-nitroanthranilic acid | 196 | 4 |
| 2-(phenylbutylamino)-5-nitroanthranilic acid | 15 | 6 |
| 2-(2-naphthylmethylamino)-5-nitroanthranilic acid | 3.5 | 8 |
| 2-(2-naphthylethylamino)-5-nitroanthranilic acid | 22.9 | 4 |
| 2-(phenylethylamino)-5-nitroanthranilic acid | 53.3 | 8 |

Further, in order to verify that 2-(arylamino)anthranilic acid compound represented by formula 1b according to the present invention has more superior chloride channel blocking activity, when compared to the anthranilic acid compound disclosed in Korean Patent Registration No. 892591, IC$_{50}$ values of several compounds were compared to one another, and results thereof are shown in Table 2 below.

TABLE 2

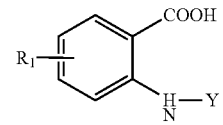

| R$_1$ | R$_3$ | * | IC$_{50}$ |
|---|---|---|---|
| 5-NO$_2$ | H | 1 | 5 |
| 5-NO$_2$ | H | 2 | 3.4 |
| 5-NO$_2$ | 4-Br | 1 | 1.5 |
| 5-NO$_2$ | 2-OMe | 1 | 9.1 |
| 5-NO$_2$ | 3-OMe | 1 | 1.8 |
| 5-NO$_2$ | 4-OMe | 1 | 2.27 |
| 5-NO$_2$ | 5-OMe | 1 | 9.2 |
| 5-NO$_2$ | 6-OMe | 1 | 1.14 |
| 5-NO$_2$ | 7-OMe | 1 | 3.4 |
| 5-NO$_2$ | 8-OMe | 1 | 8.6 |
| 5-NO$_2$ | 4-OMe | 2 | 0.038 |
| 5-NO$_2$ | 5-OMe | 2 | 18.4 |
| 5-NO$_2$ | 6-OMe | 2 | 6.7 |
| 5-NO$_2$ | 7-OMe | 2 | 1.5 |
| 5-NO$_2$ | 8-OMe | 2 | 1.3 |
| 4-NO$_2$ | 4-F | 1 | 13.6 |
| 4-NO$_2$ | 4-Cl | 1 | 4.8 |
| 4-NO$_2$ | 4-OMe | 1 | 15.2 |

| R$_1$ | R$_3$ | IC$_{50}$ |
|---|---|---|
| 5-NO$_2$ | H | 42.5 |
| 5-NO$_2$ | H | 42.5 |
| 5-NO$_2$ | 4-Br | 5.1 |
| 5-NO$_2$ | 4-OMe | 30.1 |
| 5-NO$_2$ | 4-OMe | 30.1 |
| 5-NO$_2$ | 4-OMe | 30.1 |
| 5-NO$_2$ | 4-OMe | 30.1 |
| 5-NO$_2$ | 4-OMe | 30.1 |
| 5-NO$_2$ | 4-OMe | 30.1 |
| 5-NO$_2$ | 4-OMe | 30.1 |
| 5-NO$_2$ | 4-OMe | 30.1 |
| 5-NO$_2$ | 4-OMe | 30.1 |
| 5-NO$_2$ | 4-OMe | 30.1 |
| 4-NO$_2$ | 4-F | 21.4 |
| 4-NO$_2$ | 4-Cl | 6 |
| 4-NO$_2$ | 4-OMe | 16.6 |

Referring to the results recited in Table 2 above, it can be seen that the 2-(arylamino)anthranilic acid compound represented by formula 1b according to the present invention has more excellent chloride channel blocking activity.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A chloride channel blocking agent, comprising a compound represented by formula 1b or a pharmaceutically acceptable salt compound thereof, wherein [Formula 1b] is:

wherein Y is —R$_2$ or —(CH$_2$)$_n$R$_2$ (wherein n is an integer from 0 to 6);
R$_1$ denotes nitro; and
R$_2$ is a substituted or non-substituted naphthyl group.

2. The chloride channel blocking agent of claim 1, wherein R$_2$ denotes 1-naphthyl, 2-naphthyl, 4-halo-1-naphthyl, 2-trifluoromethylnaphthyl, 4-trifluoromethylnaphthyl, 2,4-di(trifluoromethyl)naphthyl, 2,4-difluoronaphthyl, 2,6-difluoronaphthyl, 3,4-dichloronaphthyl, 4-nitronaphthyl, 4-methylnaphthyl, 4-methoxynaphthyl, 5-methoxynaphthyl, 4-nitro-2-naphthyl, 4-methyl-2-naphthyl, 1-methoxy-2-naphthyl, 4-methoxy-2-naphthyl or 5-methoxy-2-naphthyl group.

3. The chloride channel blocking agent of claim 1, wherein the compound is selected from:
compound No. 28: N-naphthyl-3-nitroanthranilic acid,
compound No. 29: N-((4-chloro)naphthyl)-3-nitroanthranilic acid,
compound No. 30: N-(2-naphthyl)-3-nitroanthranilic acid,
compound No. 31: N-naphthyl-4-nitroanthranilic acid,
compound No. 32: N-((4-fluoro)naphthyl)-4-nitroanthranilic acid,
compound No. 33: N-((4-chloro)naphthyl)-4-nitroanthranilic acid,
compound No. 34: N-((4-bromo)naphthyl)-4-nitroanthranilic acid,
compound No. 35: N-((4-nitro)naphthyl)-4-nitroanthranilic acid,
compound No. 36: N-((4-methoxy)naphthyl)-4-nitroanthranilic acid,
compound No. 37: N-(2-naphthyl)-4-nitroanthranilic acid,
compound No. 38: N-((1-methoxy)-2-naphthyl)-4-nitroanthranilic acid,
compound No. 39: N-((4-methoxy)-2-naphthyl)-4-nitroanthranilic acid,
compound No. 40: N-naphthyl-5-nitroanthranilic acid, compound No. 41: N-((4-fluoro)naphthyl)-5-nitroanthranilic acid,
compound No. 42: N-((4-chloro)naphthyl)-5-nitroanthranilic acid,
compound No. 43: N-((4-bromo)naphthyl)-5-nitroanthranilic acid,
compound No. 44: N-((4-iodo)naphthyl)-5-nitroanthranilic acid,
compound No. 45: N-((2-methoxy)naphthyl)-5-nitroanthraniic acid,
compound No. 46: N-((3-methoxy)naphthyl)-5-nitroanthranilic acid,
compound No. 47: N-((4-methoxy)naphthyl)-5-nitroanthranilic acid,
compound No. 48: N-((5-methoxy)naphthyl)-5-nitroanthranilic acid,
compound No. 49: N-((6-methoxy)naphthyl)-5-nitroanthranilic acid,
compound No. 50: N-((7-methoxy)naphthyl)-5-nitroanthranilic acid,
compound No. 51: N-((8-methoxy)naphthyl)-5-nitroanthranilic acid,
compound No. 52: N-(2-naphthyl)-5-nitroanthranilic acid,
compound No. 53: N-((1-methoxy)-2-naphthyl)-5-nitroanthranilic acid,
compound No. 54: N-((3-methoxy)-2-naphthyl)-5-nitroanthranilic acid,
compound No. 55: N-((4-methoxy)-2-naphthyl)-5-nitroanthranilic acid,
compound No. 56: N-((5-methoxy)-2-naphthyl)-5-nitroanthranilic acid,
compound No. 57: N-((6-methoxy)-2-naphthyl)-5-nitroanthranilic acid,
compound No. 58: N-((7-methoxy)-2-naphthyl)-5-nitroanthranilic acid,
compound No. 59: N-((8-methoxy)-2-naphthyl)-5-nitroanthranilic acid,
compound No. 60: N-((7-bromo)-2-naphthyl)-5-nitroanthranilic acid,
compound No. 61: N-((7-iodo)-2-naphthyl)-5-nitroanthranilic acid,
compound No. 62: N-((4-bromo)-2-naphthyl)-5-nitroanthranilic acid,
compound No. 63: N-((4-iodo)-2-naphthyl)-5-nitroanthranilic acid,
compound No. 64: N-((8-bromo)-2-naphthyl)-5-nitroanthranilic acid,
compound No. 70: N-((4-bromo)naphthyl)-6-nitroanthranilic acid,
compound No. 73: 2-(2-naphthylmethylamino)-5-nitroanthranilic acid,
compound No. 74: 2-(2-naphthylethylamino)-5-nitroanthranilic acid,
compound No. 75: 2-(phenylethylamino)-5-nitroanthranilic acid,
or pharmaceutically acceptable salts thereof.

4. A pharmaceutical composition comprising the chloride channel blocking agent or pharmaceutically acceptable salts thereof according claim 1, as an active ingredient.

5. A pharmaceutical composition comprising the chloride channel blocking agent or pharmaceutically acceptable salts thereof according claim 2, as an active ingredient.

6. A pharmaceutical composition comprising the chloride channel blocking agent or pharmaceutically acceptable salts thereof according claim 3, as an active ingredient.

7. A pharmaceutical composition comprising a compound represented by formula 1b or a pharmaceutically acceptable salt compound thereof in an amount effective for blocking a chloride channel, wherein
[Formula 1b] is:

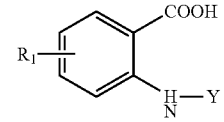

wherein Y is —$R_2$ or —$(CH_2)_n R_2$ (wherein n is an integer from 0 to 6);
$R_1$ denotes nitro; and
$R_2$ is a substituted or non-substituted naphthyl group.

* * * * *